United States Patent
Baumgartner et al.

(10) Patent No.: US 9,402,725 B2
(45) Date of Patent: Aug. 2, 2016

(54) EXPANDABLE IMPLANT

(71) Applicant: DePuy Synthes Products, Inc., Raynham, MA (US)

(72) Inventors: Adrian Baumgartner, Oberdorf (CH); Robert Frigg, Bettlach (CH); Cyril Voisard, Oberdorf (CH); Reto Nardini, Oberdorf (CH); Dieter Schmidli, Oberdorf (CH); Christian Brunner, Bern (CH); Stefan Saladin, Oberbuchsiten (CH)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/079,930

(22) Filed: Nov. 14, 2013

(65) Prior Publication Data

US 2014/0074252 A1     Mar. 13, 2014

Related U.S. Application Data

(62) Division of application No. 12/956,118, filed on Nov. 30, 2010, now Pat. No. 8,608,743.

(60) Provisional application No. 61/265,201, filed on Nov. 30, 2009, provisional application No. 61/300,734, filed on Feb. 2, 2010, provisional application No. 61/362,451, filed on Jul. 8, 2010.

(51) Int. Cl.
*A61B 17/58* (2006.01)
*A61F 2/28* (2006.01)
(Continued)

(52) U.S. Cl.
CPC ............... *A61F 2/28* (2013.01); *A61B 17/7258* (2013.01); *A61B 17/7275* (2013.01);
(Continued)

(58) Field of Classification Search
CPC ............... A61B 17/88; A61B 17/8802; A61B 17/8805; A61B 17/8833; A61B 17/8836; A61B 17/885; A61B 17/8852; A61B 17/8855; A61B 17/8858; A61B 17/7275; A61B 17/7258; A61B 17/7233
See application file for complete search history.

(56) References Cited

U.S. PATENT DOCUMENTS 4,506,681 A    3/1985    Mundell
4,525,147 A    6/1985    Pitz et al.
(Continued)

FOREIGN PATENT DOCUMENTS

CN    1308507    8/2001
CN    1376041    10/2002
(Continued)

OTHER PUBLICATIONS

U.S. Appl. No. 61/265,201, filed Nov. 30, 2009, Baumgartner et al.
(Continued)

*Primary Examiner* — Eduardo C Robert
*Assistant Examiner* — Julianna N Harvey
(74) *Attorney, Agent, or Firm* — Baker & Hostetler LLP

(57) ABSTRACT

An implant system includes a fixation device that, in turn can include an expandable implant alone or in combination with an auxiliary implant. The expandable implant includes an expandable implant body that is made from an expandable material. The expandable material includes a polymer matrix and an expandable gas source contained within at least a portion of the polymer matrix. The implant system can further include an energy source configured to heat the polymer matrix to a temperature above its glass transition temperature, thereby causing the gas source to expand inside the polymer matrix. The fixation device can further include an insertion instrument configured to implant the fixation device into an anatomical cavity.

16 Claims, 17 Drawing Sheets

(51) Int. Cl.
*A61B 17/72* (2006.01)
*A61B 17/86* (2006.01)
*A61B 17/88* (2006.01)
A61B 17/04 (2006.01)
A61B 17/74 (2006.01)
A61B 17/84 (2006.01)

(52) U.S. Cl.
CPC .............. *A61B 17/86* (2013.01); *A61B 17/866* (2013.01); *A61B 17/8858* (2013.01); *A61B 17/0401* (2013.01); *A61B 17/7266* (2013.01); *A61B 17/742* (2013.01); *A61B 17/744* (2013.01); *A61B 17/746* (2013.01); *A61B 17/848* (2013.01); *A61B 17/864* (2013.01); *A61B 17/8635* (2013.01); *A61B 17/8685* (2013.01); *A61B 2017/0409* (2013.01); *A61B 2017/8655* (2013.01)

(56) References Cited

U.S. PATENT DOCUMENTS

| | | | |
|---|---|---|---|
| 5,037,442 A | 8/1991 | Wintermantel et al. | |
| 5,163,960 A | 11/1992 | Bonutti | |
| 5,290,281 A | 3/1994 | Tschakaloff | |
| 5,662,712 A | 9/1997 | Pathak et al. | |
| 5,843,186 A | 12/1998 | Christ | |
| 5,879,387 A | 3/1999 | Jones et al. | |
| 5,972,015 A * | 10/1999 | Scribner | A61B 10/025 604/20 |
| 6,080,161 A | 6/2000 | Eaves, III et al. | |
| 6,749,556 B2 | 6/2004 | Banik | |
| 6,875,427 B1 | 4/2005 | DeVore et al. | |
| 7,182,783 B2 | 2/2007 | Trieu | |
| 7,294,187 B2 | 11/2007 | Chow et al. | |
| 7,740,656 B2 | 6/2010 | Mensah et al. | |
| 7,780,705 B2 | 8/2010 | Shaolian et al. | |
| 7,824,444 B2 | 11/2010 | Biscup et al. | |
| 7,993,404 B2 | 8/2011 | Trieu | |
| 8,608,743 B2 | 12/2013 | Baumgartner et al. | |
| 2003/0032963 A1 | 2/2003 | Reiss et al. | |
| 2003/0180344 A1 | 9/2003 | Wise et al. | |
| 2004/0030341 A1 | 2/2004 | Aeschlimann et al. | |
| 2004/0186576 A1 | 9/2004 | Biscup et al. | |
| 2004/0230309 A1 | 11/2004 | DiMauro et al. | |
| 2005/0008620 A1 | 1/2005 | Shimp et al. | |
| 2005/0090901 A1 | 4/2005 | Studer | |
| 2005/0102017 A1 | 5/2005 | Mattison | |
| 2005/0107872 A1 | 5/2005 | Mensah et al. | |
| 2005/0234289 A1 | 10/2005 | Anstadt et al. | |
| 2005/0234453 A1 | 10/2005 | Shaolian et al. | |
| 2006/0064170 A1 | 3/2006 | Smith et al. | |
| 2006/0095138 A1 | 5/2006 | Truckai et al. | |
| 2006/0229628 A1 | 10/2006 | Truckai et al. | |
| 2006/0241632 A1 | 10/2006 | Sherman et al. | |
| 2006/0241768 A1 | 10/2006 | Trieu | |
| 2006/0282166 A1 | 12/2006 | Molz et al. | |
| 2007/0027554 A1* | 2/2007 | Biran | A61L 31/146 623/23.74 |
| 2007/0123877 A1* | 5/2007 | Goldin | A61B 17/7225 606/62 |
| 2007/0233250 A1 | 10/2007 | Shadduck | |
| 2007/0270953 A1 | 11/2007 | Trieu | |
| 2008/0195227 A1 | 8/2008 | Boling et al. | |
| 2008/0269745 A1* | 10/2008 | Justin | A61B 17/7044 606/62 |
| 2009/0024161 A1* | 1/2009 | Bonutti | A61B 17/0401 606/213 |
| 2009/0054934 A1* | 2/2009 | Beyar | A61L 24/001 606/86 R |
| 2010/0241229 A1 | 9/2010 | Baehre et al. | |
| 2010/0249932 A1* | 9/2010 | Trieu | A61F 2/44 623/17.11 |
| 2011/0160870 A1 | 6/2011 | Baumgartner | |
| 2012/0041557 A1 | 2/2012 | Frigg | |
| 2012/0129131 A1 | 5/2012 | Baehre et al. | |

FOREIGN PATENT DOCUMENTS

| | | |
|---|---|---|
| CN | 1694653 | 11/2005 |
| CN | 1813032 | 8/2006 |
| CN | 1972987 | 5/2007 |
| CO | 6270194 | 4/2011 |
| EP | 0268179 | 5/1988 |
| EP | 0358601 | 3/1990 |
| EP | 0696185 B1 | 2/1996 |
| EP | 0698382 A2 | 2/1996 |
| EP | 1000958 | 5/2000 |
| EP | 1421921 | 5/2004 |
| EP | 1454602 A1 | 9/2004 |
| JP | 02-167159 | 6/1990 |
| JP | 08-506027 | 7/1996 |
| JP | 08-509642 | 10/1996 |
| JP | 09-511666 | 11/1997 |
| JP | 2004-513697 | 5/2004 |
| JP | 2006-502805 | 1/2006 |
| WO | WO 94/11058 | 5/1994 |
| WO | WO 95/28124 | 10/1995 |
| WO | WO 01/47337 | 7/2001 |
| WO | WO 02/39875 | 5/2002 |
| WO | WO 02/069817 | 9/2002 |
| WO | WO 2004/016205 A2 | 2/2004 |
| WO | WO 2006/002569 A1 | 1/2006 |
| WO | WO 2006/069677 | 7/2006 |
| WO | WO 2007/092869 A2 | 8/2007 |
| WO | WO 2008/079864 | 7/2008 |
| WO | WO 2008/112912 | 9/2008 |
| WO | WO 2009/003294 | 1/2009 |
| WO | WO 2009/013752 A2 | 1/2009 |
| WO | WO 2009/036576 | 3/2009 |
| WO | WO 2011/066522 A2 | 6/2011 |
| WO | WO 2012/021148 | 2/2012 |

OTHER PUBLICATIONS

U.S. Appl. No. 61/300,734, filed Feb. 2, 2010, Schmidli et al.
U.S. Appl. No. 61/362,451, filed Jul. 8, 2010, Baumgartner et al.
Response filed with the European Patent Office for European Patent Application No. 07 800 645.9, dated Jun. 20, 2012.
Japanese Patent Application No. 2010-513597: Office Action dated Nov. 8, 2013, 4 pages (English Translation Only).
International Application U.S. Appl. No. PCT/CH2007/000454, International Search Report mailed Jun. 17, 2008, (w/English Translation), 8 pages.
EPO Communication dated Mar. 8, 2012 for European Patent Application No. 07 800 645.9.

* cited by examiner

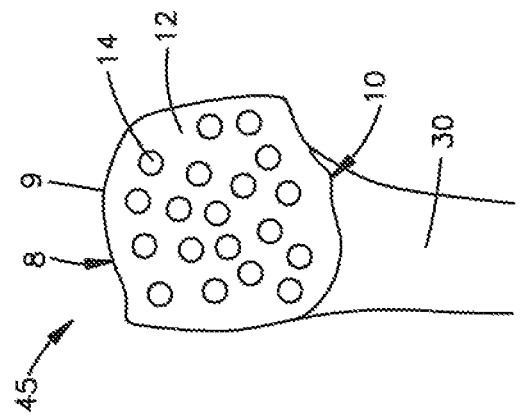
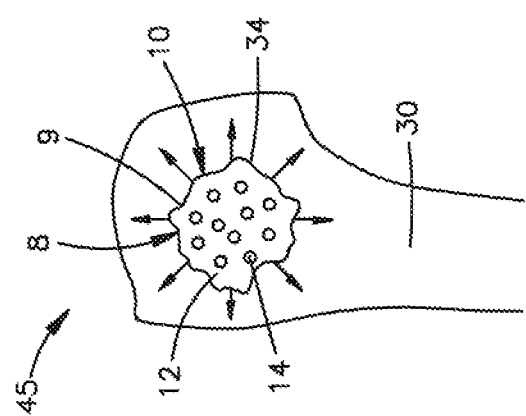

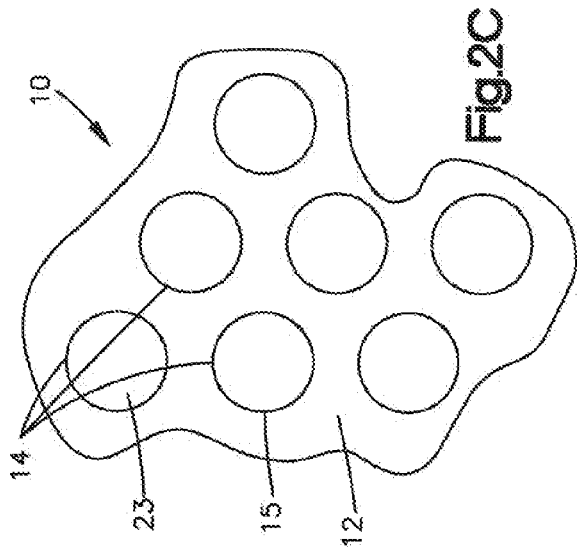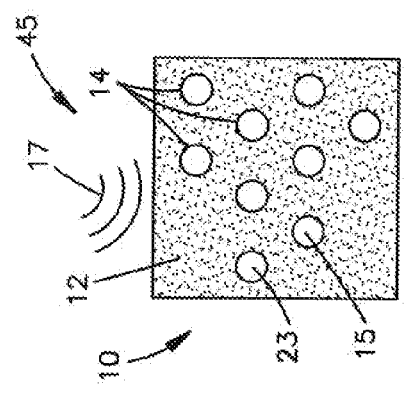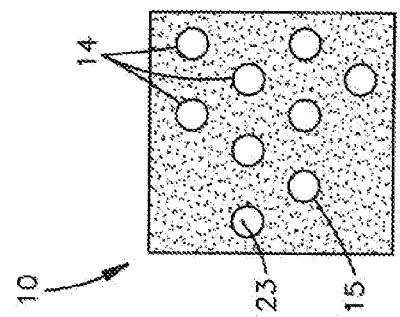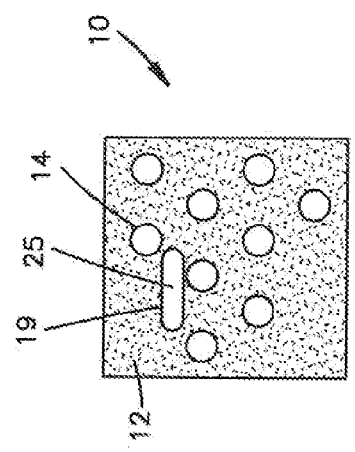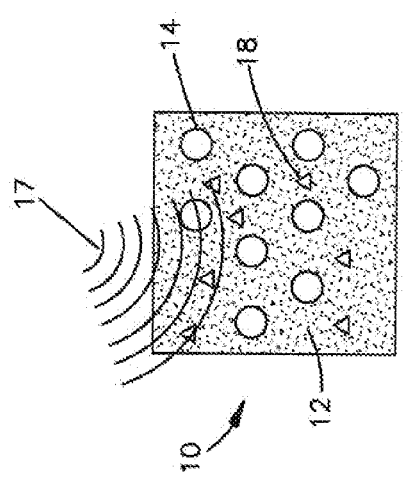

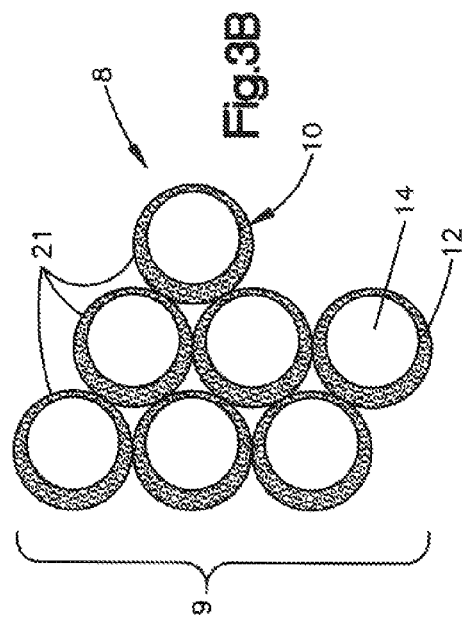
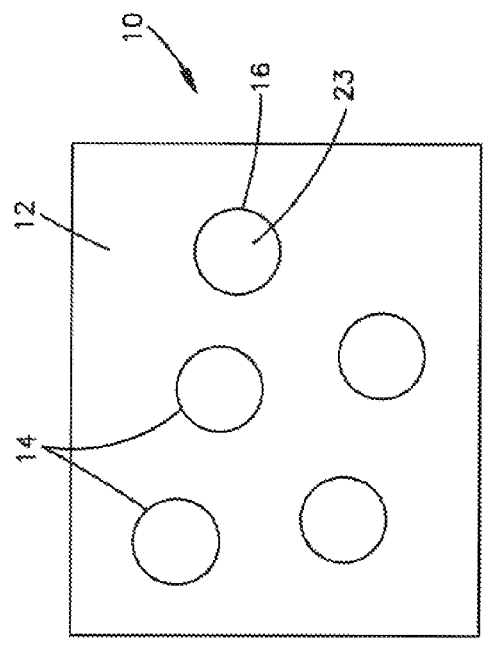
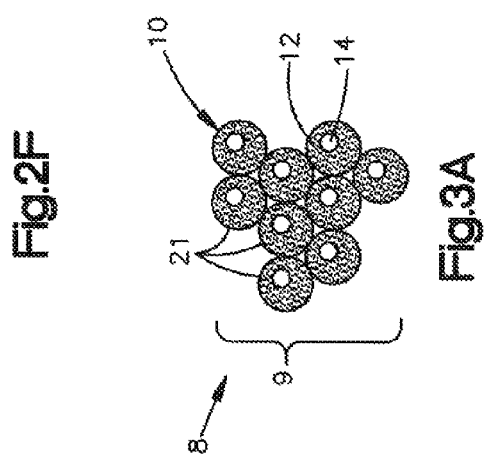
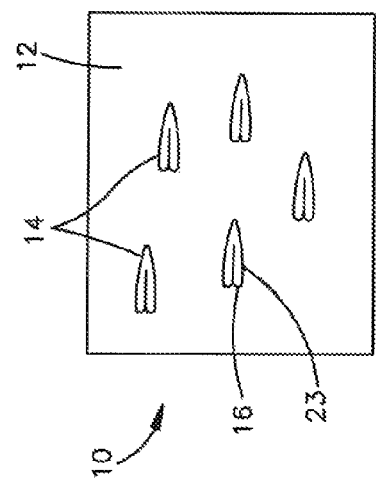

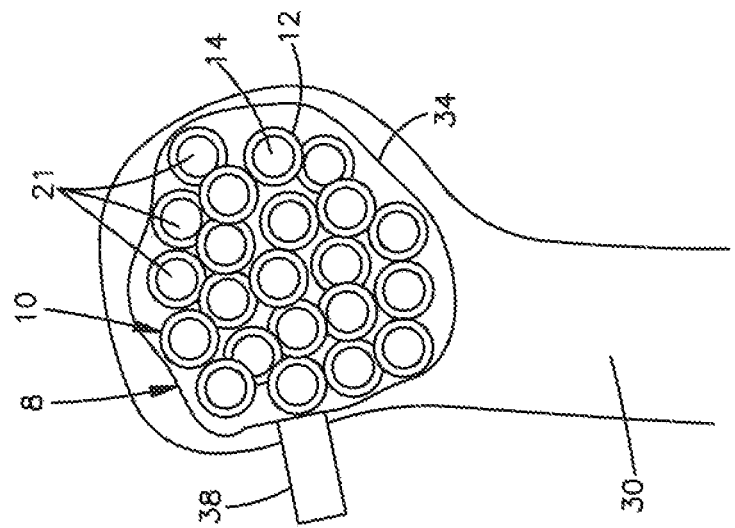
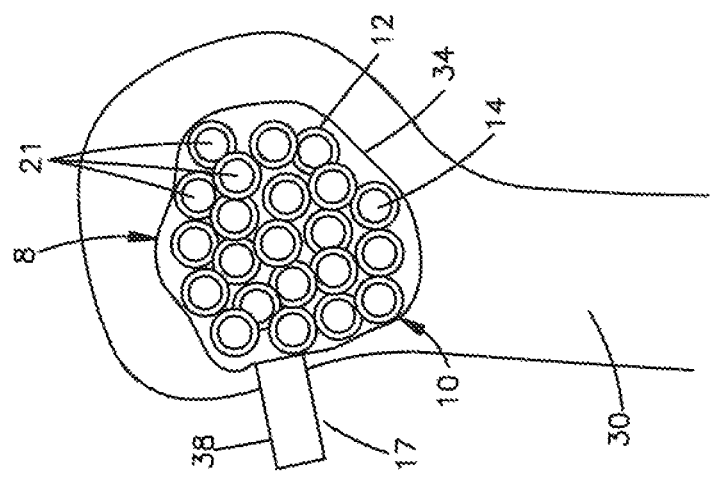
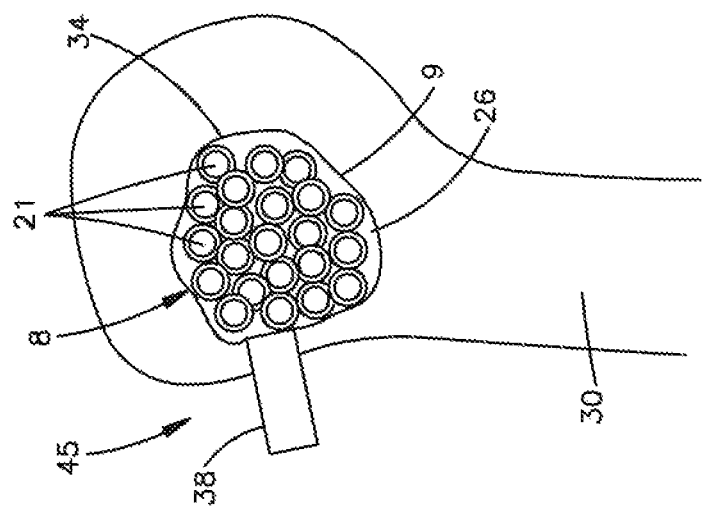

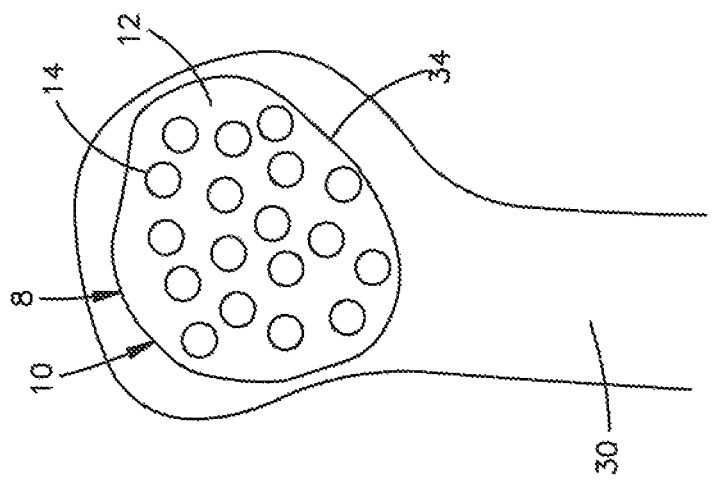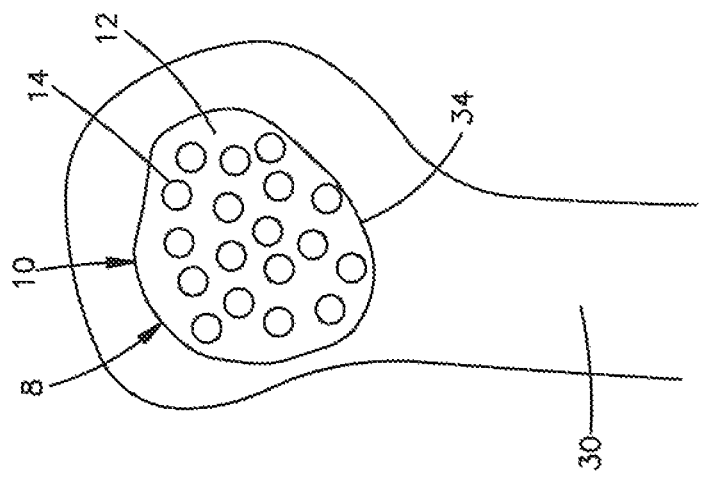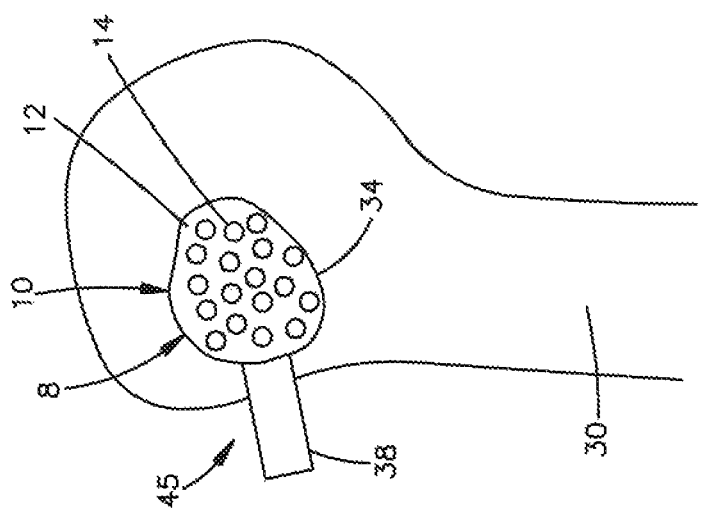

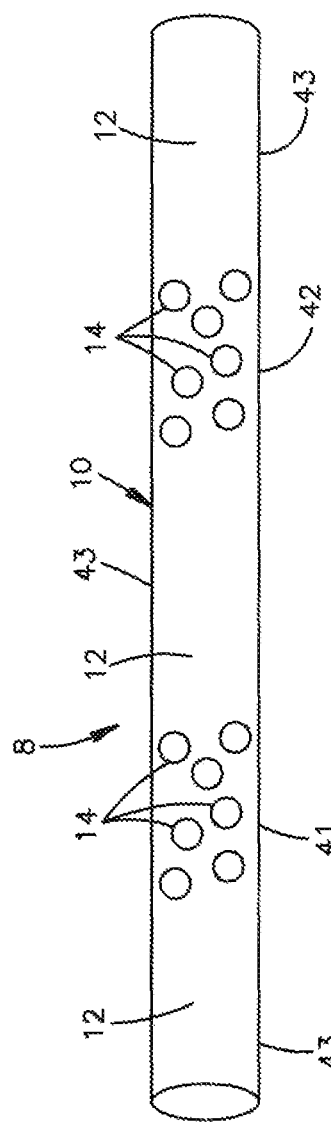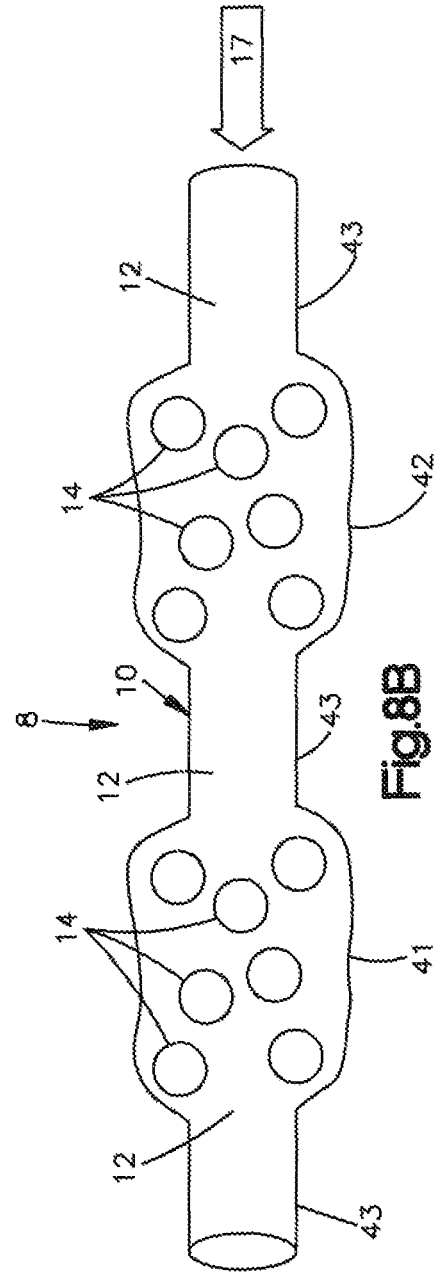
Fig.8A
Fig.8B

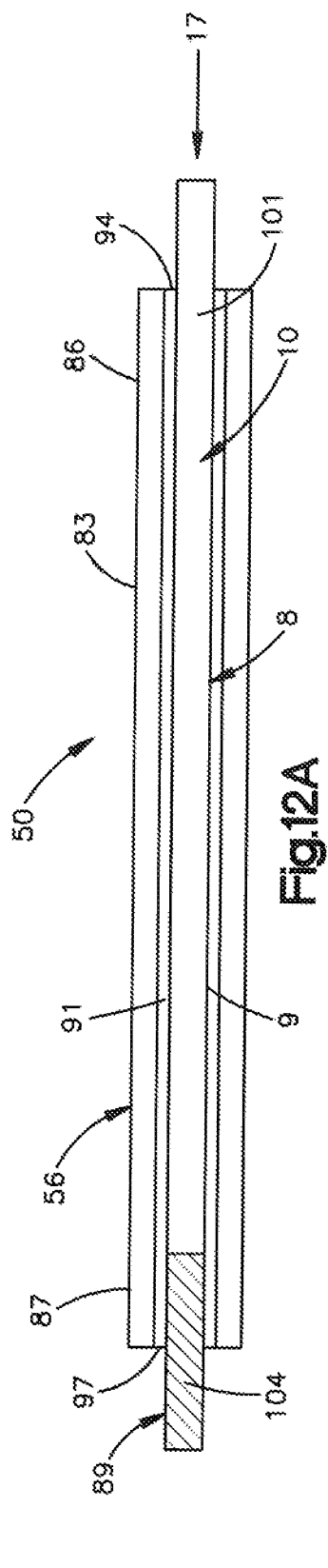
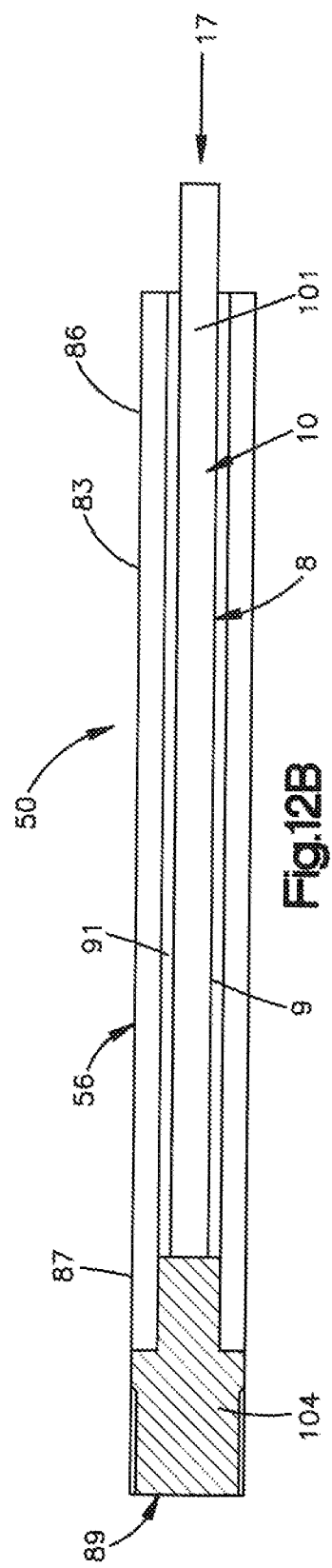
Fig.12A
Fig.12B

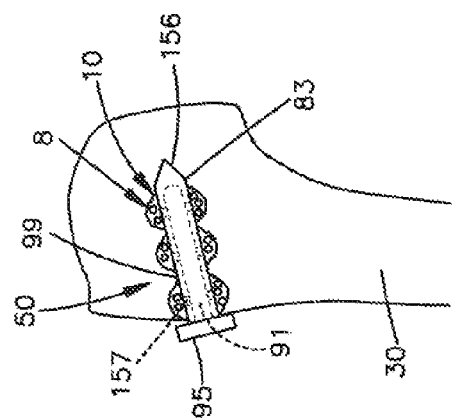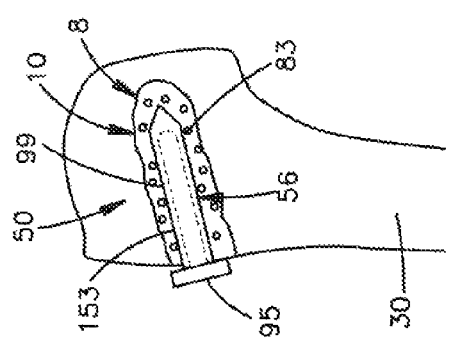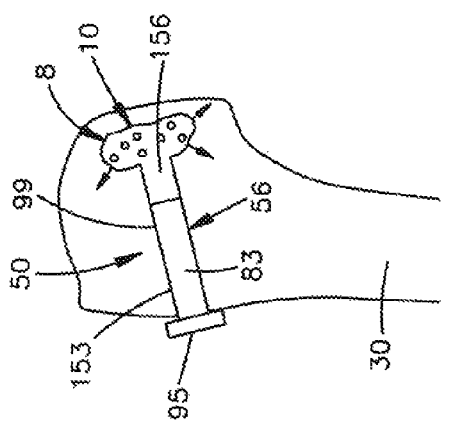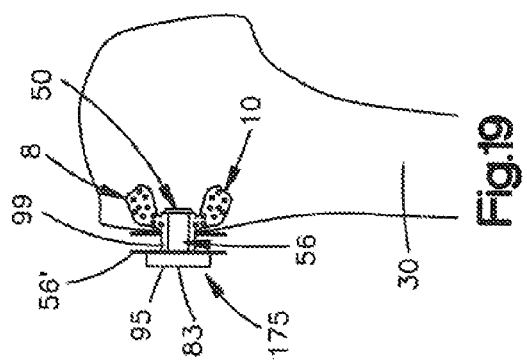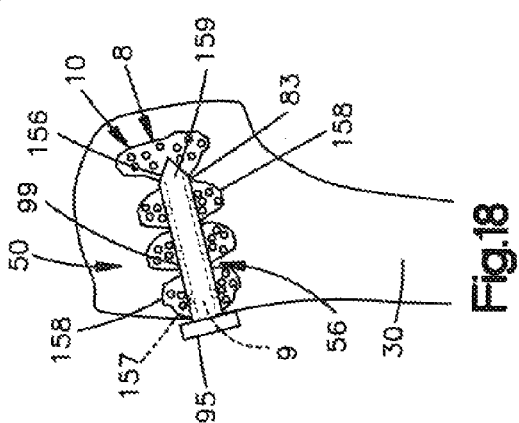

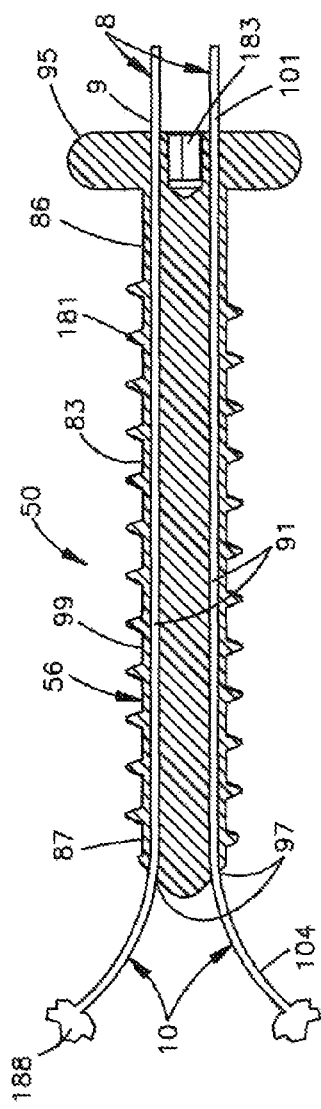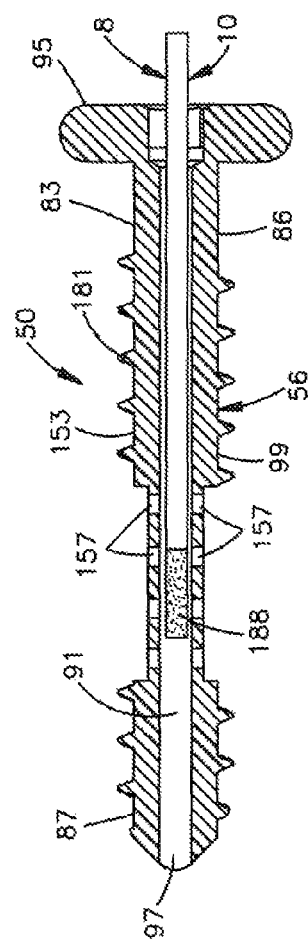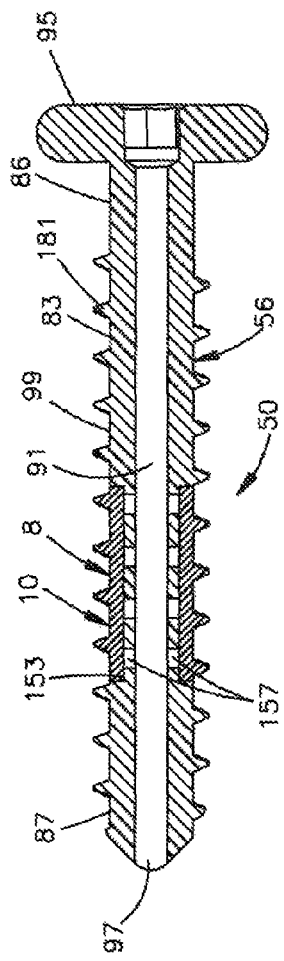

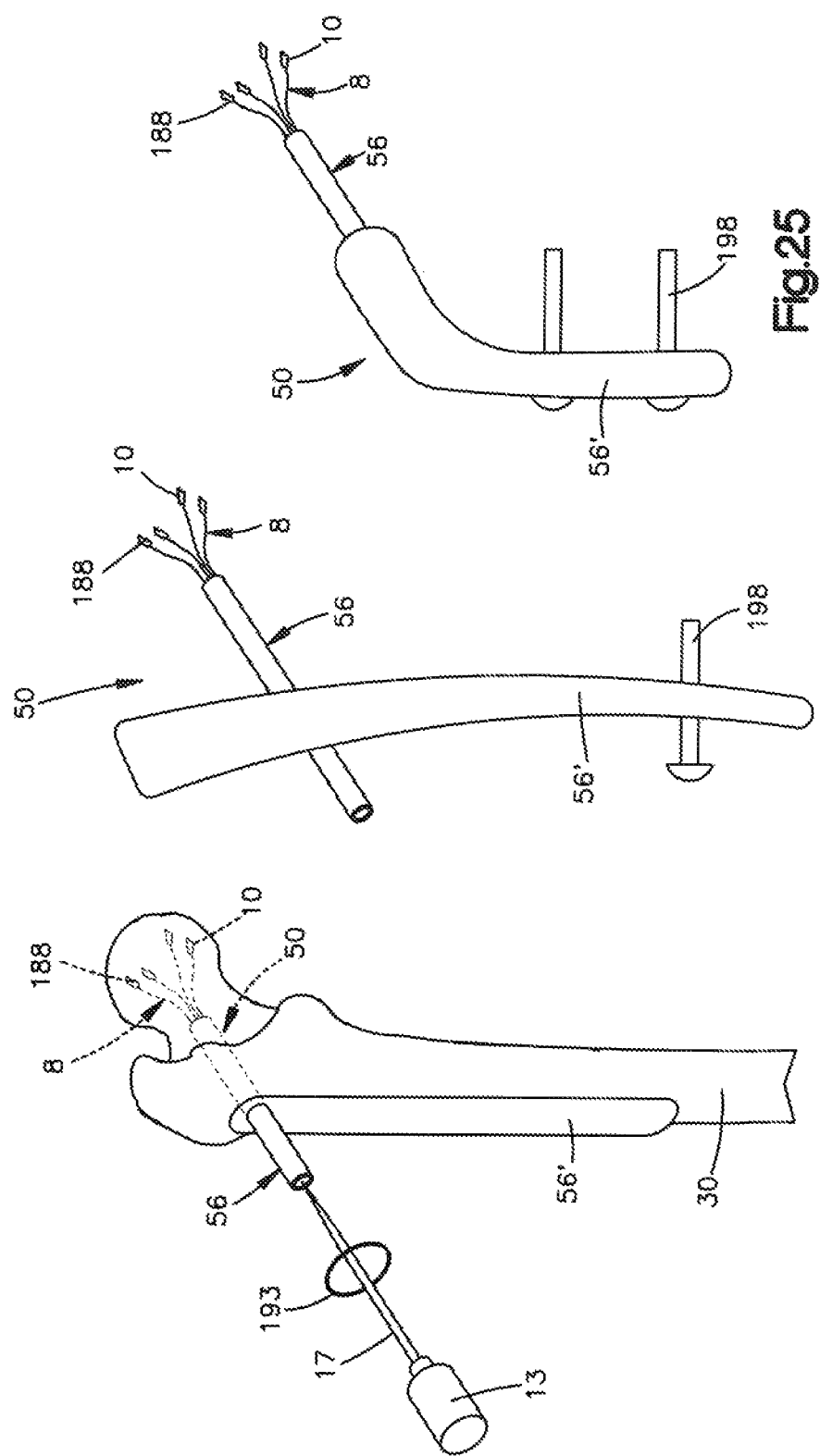

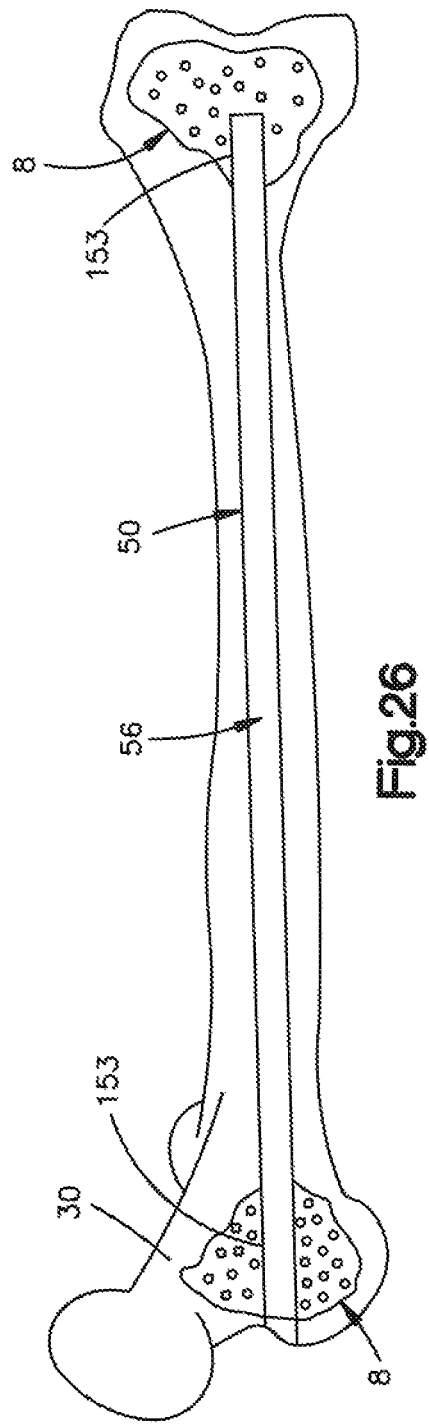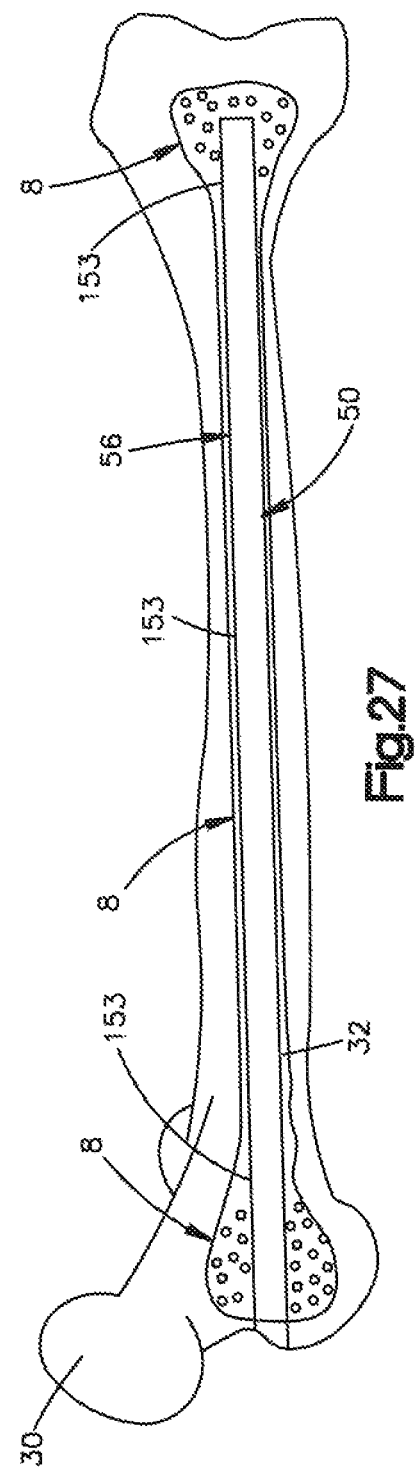

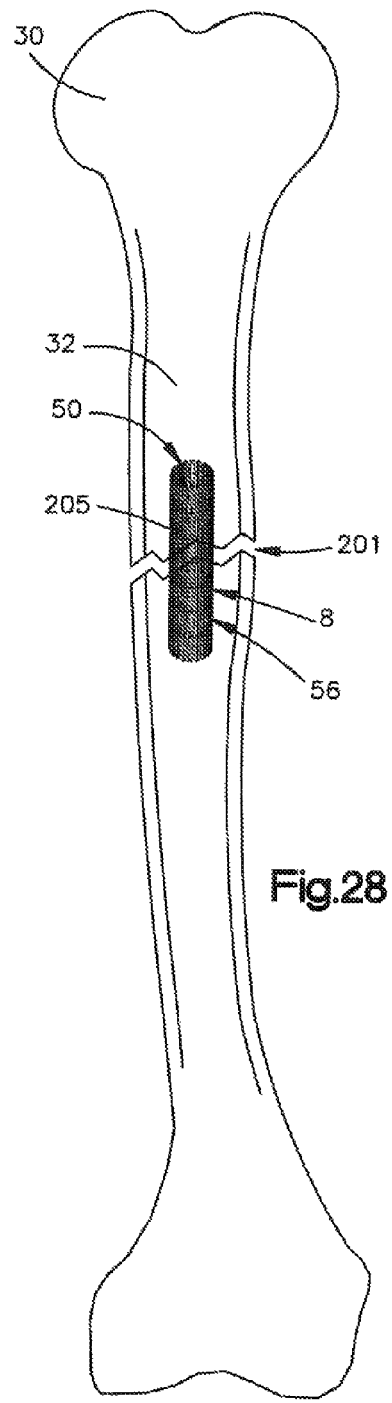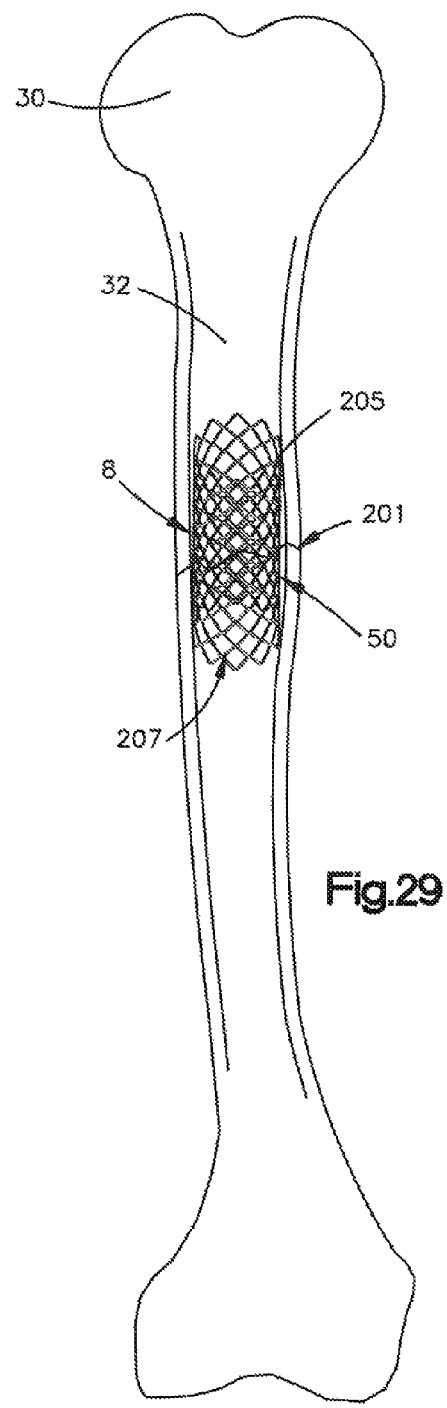

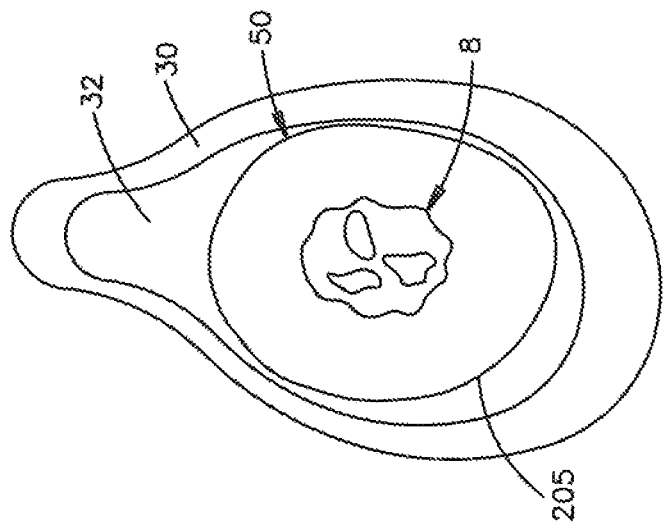
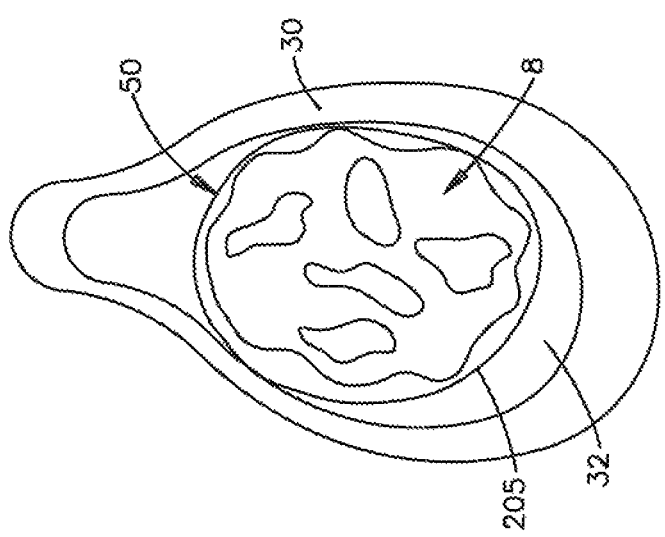
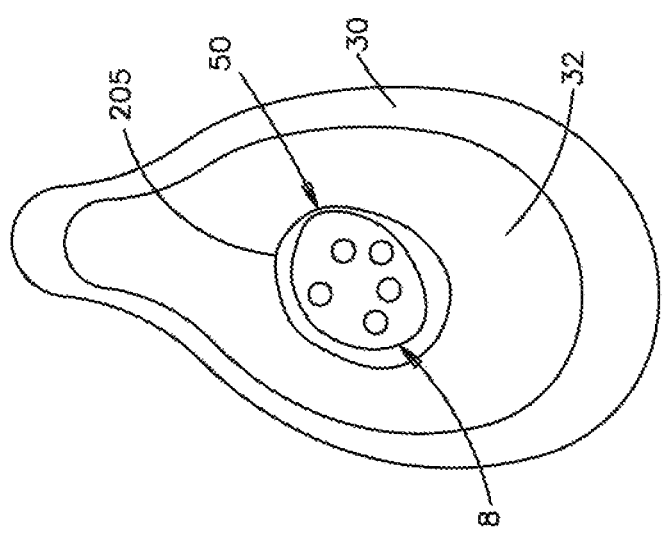

EXPANDABLE IMPLANT

CROSS-REFERENCE TO RELATED APPLICATIONS

This application is a divisional of U.S. patent application Ser. No. 12/956,118 filed Nov. 30, 2010, which claims priority to U.S. Provisional Patent Application Ser. No. 61/265,201, filed Nov. 30, 2009, U.S. Provisional Patent Application Ser. No. 61/300,734, filed Feb. 2, 2010 and U.S. Provisional Patent Application Ser. No. 61/362,451, filed Jul. 8, 2010, the disclosure of each of which is hereby incorporated by reference as if set forth in its entirety herein.

FIELD OF THE DISCLOSURE

The present disclosure generally relates to an expandable material, and more particularly relates to an implant or implants comprising an expandable material. Embodiments of the disclosure relate to a method of manufacture of the implant and to a method of expanding an expandable material.

BACKGROUND

There are different implant materials used as void fillers or to provide enhanced secondary fixation for medical implants, such as bone cements, allografts, bone grafts, i.e. bone substitute materials. Bone cements are often used as void fillers, or for fixation. A common drawback of such cements is the difficulty of removal and the difficulty to control the viscosity during injection, particularly in diaphyseal bone for joint reconstruction. As an example: In vertebroplasty the bone cement (PMMA) is mixed prior to injection. Once mixed the hardening process starts and the viscosity increases. If the viscosity it too low during injection, the cement may leave the target region (leakage) and penetrate e.g. into the spinal canal; on the other hand, if the viscosity is too high it is difficult to inject the cement.

A number of fixation devices such as screws, nails, etc. are currently used to secure bone, such as securing fractures together, or securing other devices such as plates, rods, etc. to bone. Once a fixation device is in place, unwanted movement of the device can cause problems such as damage to adjacent tissue. It is desirable to provide improved fixation devices that are easy to use, and effective at securing bone.

Thus, there remains a need for an improved implant material and an improved material to provide enhanced secondary fixation for medical implant devices.

SUMMARY

In accordance with one embodiment, and implant system includes an expandable implant that, in turn, includes an expandable implant body made from an expandable material. The expandable material can include 1) a polymer matrix, the polymer matrix made from at least one thermoplastic polymer, and 2) an expandable gas source contained within at least a portion of the polymer matrix. The polymer matrix softens when heated from a first temperature to a second temperature, such that the expandable gas source expands inside the polymer matrix thereby causing the implant body to expand from a first stable volume to a second expanded volume that is greater than the first stable volume.

BRIEF DESCRIPTION OF THE DRAWINGS

The foregoing summary, as well as the following detailed description of preferred embodiments of the application, will be better understood when read in conjunction with the appended drawings. For the purposes of illustrating the expandable implant of the present application, there is shown in the drawings preferred embodiments. It should be understood, however, that the application is not limited to the precise arrangements and instrumentalities shown. In the drawings:

FIG. 1A is a schematic elevation view of an implant system including an expandable implant having a first size and inserted into an anatomical cavity;

FIG. 1B is a schematic elevation view of the expandable implant illustrated in FIG. 1A, shown having a second size greater than the first size;

FIG. 2A is a schematic illustration of the expandable material in a first state as illustrated in FIG. 1A, including a polymer matrix and an expandable gas source disposed in the polymer matrix;

FIG. 2B is a schematic illustration of the expandable material as illustrated in FIG. 2A, shown in a transition state wherein the expandable material is exposed to an energy source that heats the polymer matrix;

FIG. 2C is a schematic illustration of the expandable material as illustrated in FIG. 2B, showing the energy source removed after the implant material has transitioned to a second state;

FIG. 2D is a schematic illustration of the expandable material similar to that illustrated in FIG. 2B, but including heat-generating particles in accordance with another embodiment;

FIG. 2E is a schematic illustration of the expandable material similar to that illustrated in FIG. 2A, but including a chemical catalyst in accordance with another embodiment;

FIG. 2F is a schematic illustration of the expandable material similar to the expandable material of FIG. 2A, but constructed with an alternative expandable gas source;

FIG. 2G is a schematic illustration of the expandable material of FIG. 2F in an expanded state;

FIG. 3A is a schematic illustration of the expandable material according to an alternative embodiment of the disclosure;

FIG. 3B is a schematic illustration of the expandable material of FIG. 3A in a second expanded state;

FIGS. 6A-6C are schematic elevation views showing selected steps of a method for implanting an expandable implant into bone in accordance with another embodiment;

FIGS. 7A-7C are schematic elevation views showing selected steps of a method for implanting an expandable implant into bone in accordance with yet another embodiment;

FIG. 8A is a schematic elevation view of an expandable implant constructed of an expandable material according to one embodiment in a first stable state;

FIG. 8B is a schematic elevation view of the implant of FIG. 8A in a second expanded state according to one embodiment;

FIG. 12A is schematic elevation view of a bone fixation device in the form a of a Kirschner wire including an expandable implant having a dyed portion is at a first stable volume according to one embodiment;

FIG. 12B is a schematic elevation view of the bone fixation device of FIG. 12A where the dyed portion of the expandable implant is at a second expanded volume according to one embodiment;

FIGS. 15-19 are schematic elevation views of bone fixation devices inserted into an underlying bone, whereby the fixation devices include an expandable implant and an auxiliary implant in accordance with various embodiments;

FIGS. 20-22 are side elevation views of bone fixation devices, whereby the fixation devices include an auxiliary implant shaped substantially as a bone screw and an expandable implant in accordance with various embodiments;

FIG. 23 is a schematic elevation view of a bone fixation device whereby the fixation device includes an auxiliary implant shaped substantially as a bone screw and an expandable implant in accordance with one embodiment;

FIG. 24 is a schematic elevation view of a bone fixation device whereby the fixation device includes an auxiliary implant shaped substantially as a bone screw and an expandable implant in accordance with another embodiment;

FIG. 25 is a schematic elevation view of a bone fixation device whereby the fixation device includes an auxiliary implant shaped substantially as a bone screw and an expandable implant in accordance with a further embodiments;

FIGS. 26 and 27 are schematic elevation views of a bone fixation device whereby the fixation device includes an auxiliary implant shaped substantially as an intramedullary nail disposed in a bone canal, and an expandable implant in accordance with an embodiment;

FIG. 28 is a schematic elevation view of a bone fixation device whereby the fixation device includes an auxiliary implant shaped substantially as an intramedullary stent and an expandable implant in accordance with an embodiment;

FIG. 29 is a schematic elevation view of the device of FIG. 28, shown in a second expanded state;

FIG. 30 is a cross-sectional view of the device of FIG. 28;

FIG. 31 is a cross-sectional view of the device of FIG. 29;

FIG. 32 is a cross-sectional view of the device of FIG. 28 showing partial resorption of the expandable implant.

DETAILED DESCRIPTION

Figure 4C:
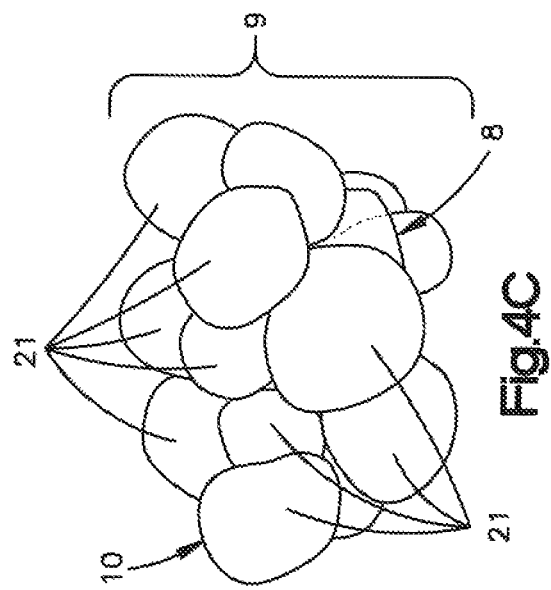
FIG. 4C is a schematic elevation view of the expandable implant of FIG. 4B after expansion from the transition state to a second expanded state.

Referring to FIGS. 1A-1B. an implant system 45 includes an expandable implant 8 that is configured to be inserted into an anatomical cavity 34, for instance of a bone 30. For example, the anatomical cavity can include a vertebral space, an intramedullary space, or other anatomical space internal to a bone or between adjacent bones or bone segments. As shown in FIG. 1A, the expandable implant 8 includes an implant body 9 that is made of an expandable material 10. The implant body 9 is configured to be disposed in the cavity 34 when the implant material 10 is in a first state. For instance, the implant 8 can be inserted (e.g., injected or otherwise positioned) into the cavity 34. When the expandable material 10 is in the first state, the implant body 9 defines a first size, which can be a stable volume. When the implant body 9 defines the first size, the implant body 9 can define any suitable shape as desired so that the implant body 9 can fit within the anatomical cavity 34. For instance, the implant body 9 can define a rectangular, a square, a bar shape, a flat sheet, a cylindrical body, or other convenient starting geometry as desired.

The expandable material 10, and thus the implant body 9, is adapted to expand to change shape and/or volume as will be described in embodiments below. Accordingly, once the implant 8 is disposed in the cavity 34, the implant body 9 can be expanded from the first size to the second size, which can be referred to as a second expanded volume. In particular, the expandable material 10 can be activated and heated from the first state to a transition state, and subsequently to a second state. As the expandable material 10 is activated and heated from the first state to the transition state, the expandable material 10 and thus implant body 9 softens and is configured to conform geometrically to a corresponding geometric shape of the cavity 34 to the second expanded volume, thereby providing a contoured fit within the cavity 34. The expandable material 10, and thus the implant body 9, can then cool and harden upon a removal of heat from the transition state to the second state, whereby the implant body 9 defines the second expanded volume. The implant body 9 is configured to retain its expanded second volume when the expandable material 10 is cooled and re-hardened. Because the expandable material 10 can remain in a first stable state prior to activation, the user is provided with time flexibility when inserting the implant 8 in the cavity 34 before the expandable material 10 is activated.

Referring also FIG. 2A, the expandable material 10 includes a polymer matrix 12 and an expandable gas source 14 disposed in the polymer matrix 12. It should be appreciated that the polymer matrix 12 can transition from a first state in which the polymer matrix 12 resists expansion to a second state in which the polymer matrix can be expanded, for instance by the expandable gas source that expands inside the polymer matrix 12, thereby causing the implant body 9 to expand from a first stable volume to a second expanded volume that is greater than the first stable volume. In accordance with one embodiment, the polymer matrix 12 includes a thermoplastic polymer or mixture of different thermoplastic polymers. The polymer matrix 12 can have a glass transformation range such that in the first state it has a viscosity or stiffness that resists expansion of the expandable gas source 14. When the expandable material 10 is heated to a temperature that causes the polymer matrix 12 to transition from the first state to the second state, it has a second viscosity or stiffness that allows the expandable gas source 14 to expand the polymer matrix 12 while remaining cool enough to avoid causing heat-related damage to surrounding tissue. wherein the polymer matrix. The polymer matrix 12 could include any suitable bioresorbable polymer, such as polylactide polymers, or can include a non-bioresorbable polymer as desired. For example, the polymer matrix could include polycaprolactone (PCL) or it could include polylactide (PLA).

PCL has the glass transition temperature ($T_g$) in the region of −60° C. and a melting temperature ($T_m$) in the region of 60° C. Where the polymer matrix 12 includes PCL, at room temperature (approximately 25° C.), the PCL is in the first state and when the polymer matrix is heated to a temperature of around 50° C., the PCL is in the second state.

PLA has a transition temperature ($T_g$) in the region of 58° C. and a melting temperature ($T_m$) in the region of 175° C. Where the polymer matrix 12 includes PLA, at room temperature (approximately 25° C.), the PLA is in the first state and when the polymer matrix is heated to a temperature of around 65° C., the PLA is in the second state.

In one embodiment, the expandable gas source 14 can be configured as at least one compressed bubble 15 such as a plurality of bubbles 15 of gas 23 trapped within the polymer matrix 12. In one example, the gas 23 in the compressed bubbles 15 can include a carbon dioxide gas. Carbon dioxide has a sufficiently low diffusion rate through the polymer matrix 12, such that the pressure of gas 23 is substantially maintained over time prior to activation of the expandable material 10. It should be appreciated, however, that the gas 23 can be provided as desired, such as compressed air, inert gasses, or any suitably compressible gas. Thus, the polymer matrix 12 encapsulates the expandable gas source 14 in its compressed configuration when the expandable material 10 is in the first state at a first stable temperature.

As illustrated in FIG. 2A, the expandable gas source 14 can be distributed as desired. For example, the expandable gas source 14 can be substantially homogenously distributed throughout the polymer matrix 12, can alternatively be more concentrated in one or more portions of the polymer matrix 12. In some embodiments, one or more portions of the polymer matrix 12 can be devoid of the expandable gas source 14 to provide differential expansion as will be described in more detail below. Also, although the polymer matrix 12 is shown as substantially continuous for illustration purposes, in selected examples, the polymer matrix 12 has an internal open pore polymer matrix in which the bubbles 15 that include the expandable gas source 14 are interconnected.

Referring to FIG. 2B, the implant system 45 can further include any suitable energy emitting device as desired (see, e.g., laser 13 illustrated in FIGS. 5D and 23) that is configured to apply a corresponding energy source 17 to the expandable material 10 that causes the temperature of the polymer matrix 12 to increase and soften as the expandable material 10 transitions from the first state to the transition state. As the polymer matrix 12 softens, the expandable gas source 14, such as bubbles 15 of compressed gas 23 can expand within the polymer matrix 12, thereby expanding the implant body 9 as described above with respect to FIGS. 1A-B.

Heating of the expandable material 10 with an energy source 17 can be performed by any method as desired. Suitable energy sources can include, for example, electrical resistive heating through a wire or other conductor, ultrasonic friction heating, radiant heating paramagnetic particle heating, heated fluid exchange and chemical heating, as well as utilizing electromagnetic energy or irradiation including the use of lasers or visible or UV light sources. Although several example energy sources 17 that can transfer energy to heat the expandable material 10 have been described, any suitable energy source 17 for heating the expandable material 10 can be used as desired.

FIG. 2C shows the expandable material 10 in an expanded state. After heating the expandable material 10 to the desired second temperature, the polymer matrix 12 softens, allowing the expandable gas source 14 to expand and exert a force on the polymer matrix 12 causing the expandable material 10 to increase in volume to a second expanded volume greater than the first stable volume as shown in FIG. 2C. In one example the second temperature is high enough to soften the polymer matrix 12, and yet low enough to not significantly damage surrounding tissue or bone. An expandable material 10 as described above in FIG. 2A is stable at the first temperature and has a stable first volume. In one example, where the polymer matrix includes PLA, as set out above, the first temperature is below the glass transition temperature of the polymer matrix 12. At the first temperature, the expandable gas source 14 is inactive and/or is contained due to the mechanical properties of the polymer matrix 12. The expandable material 10 will remain substantially at the first stable volume until thermally activated. Once energy is applied to the expandable material 10 from the energy source 17, the expandable material 10 is heated to a transition state and transitions from the first temperature to a second temperature. In one example, the second temperature is greater than the glass transition temperature of the polymer matrix 12. At that second temperature, the polymer matrix 12 including PLA, softens, allowing the expandable gas source 14 to expand and exert a force on the polymer matrix 12 causing the expandable material 10 to increase in volume to a second expanded volume greater than the first stable volume.

When the energy source 17 is provided as ultrasonic wave energy or ultrasonic vibration that is applied to the expandable material 10, the wave energy causes the expandable material 10 to vibrate and the resulting friction within the expandable material 10, which can be provided by the polymer matrix 12 and/or the gas 23, causes the temperature of the polymer matrix 12 to increase from a first temperature to a second temperature at which polymer chains in the polymer matrix 12 can move more freely relative to each other and the expandable material 10 is able to increase in volume to the second expanded volume. It should be appreciated that ultrasonic vibration can used to heat the expandable material 10 by internal friction caused by particles within the expandable material 10 that vibrate at an ultrasonic resonance frequency.

Another example of an energy source 17 includes a light source such as visible or UV light, or a laser source. In one embodiment, the expandable material 10 further includes a sensitizer such as a dye that is capable of absorbing light and converting the light energy to heat when exposed to a light source. The dye can be homogenously distributed throughout the expandable material 10. Alternatively, the dye can be concentrated in one or more portions of the expandable material 10 and correspondingly absent from other portions of the expandable material 10. As an example, a dyed portion of an expandable material absorbs light more than a clear or light colored portion of an expandable material. Clear expandable materials tend to pass light through, and white or otherwise light color expandable materials tend to reflect light in contrast to absorption. Other examples of sensitizers include chemicals that react to a selected wavelength of light. In one example the sensitizer such as a dye is mixed only in the polymer matrix 12. In another example the sensitizer is included in only a selected portion or portions of the expandable material 10 to provide directed expansion of the implant 8 at an expansion region or regions of the implant body 9. In a further example, the sensitizer can be contained within the expandable gas source 14. In selected light source embodiments, the light interacts with the sensitizer described above to induce heating of the expandable material 10. In one example, the sensitizer is a dye included in a portion of the expandable material 10. Laser light preferentially heats the dyed portion of the expandable material 10. An advantage of heating by an energy source 17, such as a light source, includes the ability to heat the expandable material 10 without direct physical contact. Another advantage of heating by a light energy source 17 using a sensitizer, such as a dye, includes the ability to heat only a selected portion (for example a dyed portion) of an implant body 9.

In another example, energy source 17 includes electromagnetic wave energy that is used to excite all, or a portion, of the expandable material 10 remotely. FIG. 2D illustrates an example where the expandable material 10 further includes a number of heat-generating particles 18 that react to produce heat in the presence of an electromagnetic field. The particles 18 are shown within the expandable material 10. In one embodiment, the particles 18 include paramagnetic particles. The particles 18 are shown in block diagram form as triangles in FIG. 2D for illustration only. The particles 18 absorb energy from an energy source 17, such as electromagnetic waves when in the presence of a generated alternating electromagnetic field. The energy absorbed by the particles 18 is converted to heat, and transferred to the expandable material 10 raising the temperature of the expandable material 10 from the first temperature to the second temperature. In one example, the particles 18 include superparamagnetic iron oxide ($Fe_3O_4$) particles. In one example, the iron oxide particles are nanoscale particles. One advantage of inducing activation by electromagnetic wave energy is that physical contact with the expandable material 10 is not necessary, as for example with resistance heating. Only close proximity to the electromagnetic field is required.

In an alternative embodiment, the energy source 17 can be included within the expandable material 10. For example, the expandable material 10 can be heated by release of a chemical catalyst 25 from one or more capsules 19 or other containers mixed within the expandable material 10. FIG. 2E illustrates the expandable material 10 with a polymer matrix 12 and an expandable gas source 14 as described in embodiments above. A catalyst capsule 19 filled with a chemical catalyst 25 is also included. Although one large capsule 19 is shown for illustration, any number of capsules and a variety of capsule sizes are possible within the scope of the disclosure. In operation, the expandable material 10 is squeezed or otherwise mechanically deformed to break the capsule 19 or capsules. The catalyst 25 contained within then begins a reaction that heats and softens the expandable material 10 or otherwise activates the expandable gas source 14. In one example a chemical reaction initiated by the chemical catalyst 25 is an exothermic reaction that heats the expandable material 10 to soften the polymer matrix 12.

In another example, the expandable gas source 14 is activated by the change in pH level inside a body. In such an example the polymer matrix 12 of the expandable material 10 is stable at a pH level of a typical environment outside a body. A chemical reaction is activated to heat the expandable material 10 or otherwise activate the expandable gas source 14 once the expandable material is exposed to the different pH level within a body.

According to a further aspect of the present disclosure, a method is provided for manufacturing the expandable material. The method includes one or more, up to all, of the following steps:

heating a polymer matrix to a temperature sufficient to soften the polymer matrix;

introducing a gas into the polymer matrix while under an elevated external pressure; and, cooling the polymer matrix while under the elevated external pressure to a temperature that hardens the material and entraps the pressurized gas as an expandable gas source within the polymer matrix.

In such a method of manufacture as described above, the elevated external pressure constrains the volume of the gas to a reduced volume than it would otherwise be a normal atmospheric pressure. Further, cooling the polymer matrix while under the external pressure entraps the gas at a non-equilibrium volume.

Referring to FIGS. 2F and 2G, expandable material 10 includes a polymer matrix 12 with an expandable gas source 14 including a distribution of gas capsules 16 formed from a from a shape memory polymer (SMP). SMPs are polymeric materials that have the ability to return from a deformed state (temporary state) to their original state (permanent state) upon activation from an external stimulus or trigger, such as a temperature change. In FIG. 2F, the SMP capsules 16 are locked in a first deformed geometry that holds a contained gas 23 as an expandable gas source 14. Once activated by an energy source, the expandable material 10 heats and softens the polymer matrix 12, permitting the SMP capsules 16 to expand from a deformed state to a remembered shape state with a larger volume. FIG. 2G shows the SMP capsules 16 returned to a remembered shape. The larger volume of the activated SMP capsules 16 produces expansion in the expandable material 10.

In an alternative embodiment, the expandable gas source 14 includes a chemical mixture that is capable of forming gas bubbles. In one example, the chemical mixture is activated, but contained within the polymer matrix 12 due to mechanical properties of the polymer matrix 12 at a first stable temperature as discussed above, and at a second elevated temperature exerts an expansive force on the polymer matrix 12, expanding the expandable material. In another example the chemical mixture is non-reactive at a first stable temperature, and is activated by raising the expandable material 10 to a second temperature. At the second temperature, the chemical mixture of the expandable gas source 14 begins to form gas bubbles 15 that expand to provide expansion of the expandable material 10.

One example of chemical mixture suitable as an expandable gas source 14 is baking soda (sodium bicarbonate, $NaHCO_3$), an acid salt, and optionally, an inert starch. This mixture is typically known as baking powder. In one embodiment the acid salt is a slow acting acid salt that is only activated at an elevated temperature. One example of a slow acting acid salt includes disodium diphosphate (sodium acid pyrophosphate $Na_2H_2P_2O_7$). A gas formed by such a chemical reaction includes carbon dioxide gas. The chemical mixture can further include a sensitizer, as previously described, for example a dye that is capable of interacting with a light energy source such as a laser to provide heating of the expandable material 10.

According to another aspect of the present disclosure, the method for manufacturing the expandable material can include one or more, up to all, of the following steps:
heating a polymer matrix to a temperature sufficient to soften the polymer matrix;
introducing a chemical mixture capable of generating gas at an activation temperature into the polymer matrix;
cooling the polymer matrix to a temperature that hardens the material and entraps the chemical mixture as an expandable gas source within the polymer matrix.

Referring to FIG. 3A an expandable implant 8 can include an implant body 9 having a plurality of expandable particles 21 such as beads. Although the expandable particles 21 are shown as substantially round for illustration, the actual shape of expandable particles 21 may vary. At least one up to all expandable particles 21 can be made from an expandable material 10 having a polymer matrix 12 and an expandable gas source 14 as described above. In FIG. 3A, expandable implant 8 is in a first stable state prior to activation of the expandable material 10. An example of a thermoplastic polymer that can be utilized as the polymer matrix 12 of expandable particle 21 is polystyrene. FIG. 3B illustrates the expandable particles 21 after activation of the expandable material where the polymer matrix 12 has been softened and the expandable particles 21 have expanded such that expandable implant 8 is at a second expanded state due to expansion of the expandable gas source 14. Expandable particles 21 can be combined with a carrier material to form a paste that can be shaped or otherwise formed or alternatively combined with a carrier fluid that would allow for injection of the expandable material 20.

Figure 4B:
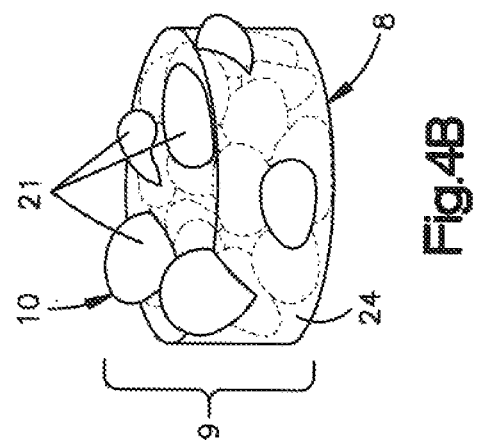
FIG. 4B is a schematic elevation view of the expandable implant of FIG. 4A in a transition state from the first stable state after activation from an energy source.
Figure 4A:
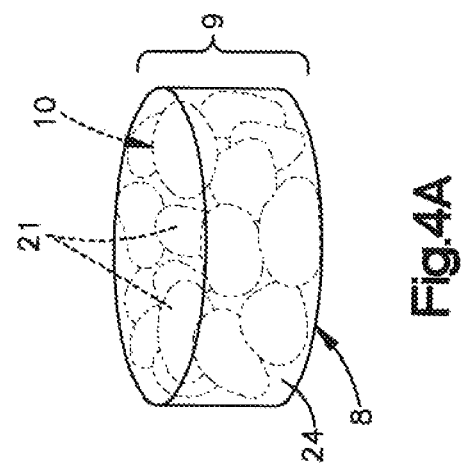
FIG. 4A is a schematic elevation view of an expandable implant constructed of the expandable material in a first stable state.

FIG. 4A shows expandable implant 8 having an implant body 9 including a plurality of expandable particles 21 and a polymerized material 24. Expandable particles 21 are fixed within the polymerized material 24 such that the implant body 9 is at a first stable volume and expandable gas source 14 (not shown) is in a compressed state. FIG. 4B shows activation of the expandable material 10 from the first state to a transition state including the initiation of expansion of the expandable particles 21 from a first stable volume upon heating in a manner as described above. FIG. 4C shows the expandable implant 8 where implant body 9 has expanded to a second expanded volume due the expansion of expandable particle 21 as described above. After the particles 21 cool, the implant body 9 can maintain its second expanded volume.

According to an additional aspect of the disclosure a method of manufacturing the expandable material 20 includes:
compressing a plurality of expandable particles having a polymer matrix and an expandable gas source from an initial volume to a compressed volume;
surrounding the expandable particles with a polymerizable material; and
polymerizing the polymerizable material such that the expandable particles are constrained by the polymerizable material in the compressed volume and the expandable gas source is in a compressed state.

According to this particular method of manufacture, expandable particles 21 can be compressed from an initial volume under external pressure and heat to a compressed volume. The compressed expandable particles 21 can then be surrounded or otherwise coated with a polymerizable material that is subsequently polymerized forming an expandable implant 8. The expandable implant 8 is then cooled under external pressure and the polymerized material 24 entraps the expandable particles 21 in a first stable volume with the expandable gas source 14 in a compressed state. Upon application of an energy source to the expandable material 10, the expandable implant 8 will behave in the manner described above, i.e., it will undergo heating, softening, and expansion to a second expanded volume.

Referring to FIGS. 5A-5D the implant system 45 can include the expandable implant 8, constructed in accordance with any suitable embodiment as described herein for filling an anatomical cavity, and an insertion instrument 38. A bone 30 is used as an example anatomical location having a cavity 34 that receives, and can be at least partially or entirely filled by, the implant 8. The insertion instrument 38 is configured to contain an expandable implant 8 including the expandable material 10 coated on a distal end. Alternatively, the insertion instrument 38 can be configured in the form of hollow pin or syringe that can contain the expandable implant 8 within a passage or channel in the insertion instrument 38. The distal end is inserted into the cavity 34 of the bone 30 such that the expandable implant 8 is position in the cavity 34 at a first stable volume.

Figure 5A:
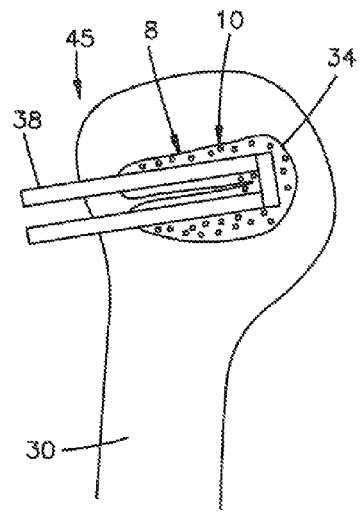
FIGS. 5A-5C are schematic elevation views showing selected steps of a method for implanting an expandable implant into bone in accordance with one embodiment.
Figure 5B:
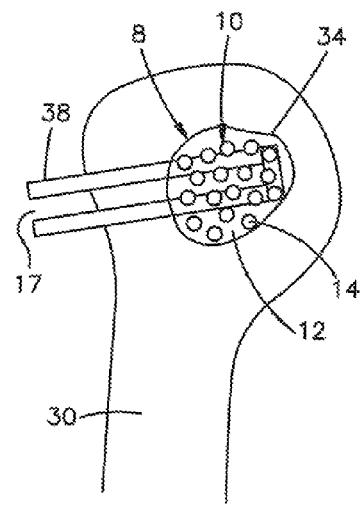

The instrument 38 can be coupled to an energy device 13 that is configured to transmit an energy source 17 to the expandable implant 8, and heat the expandable material 10. For example, energy source 17 may be configured as a heated fluid exchanger where heated fluid may flow through passages in a heat exchanger that is coupled to the insertion instrument 38. The energy device 13 shown in FIG. 5D is a battery powered laser device. In FIG. 5B, the energy source 17 has been activated, resulting in the expandable material progressing from a first stable state to a transition state, such that the polymer matrix 12 is softened and the expandable gas source 14 initiates expansion.

Figure 5C:
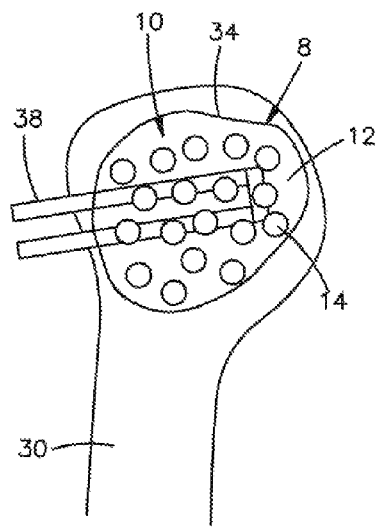
Figure 5D:
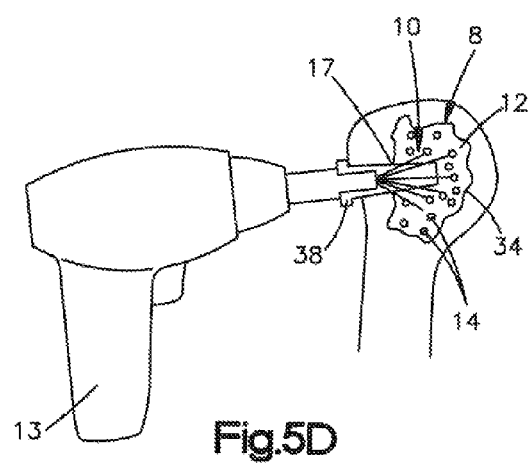
FIG. 5D is a schematic elevation view showing a battery powered laser device used as an energy device for expanding the expandable implant according to the method steps shown in FIGS. 5A-5C.

In FIG. 5C, the expandable gas source 14 is shown in an expanded state within a polymer matrix 12. The expandable implant 8 expands to a second expanded volume and can fill the cavity 34 to a greater extent than in its previous first stable volume, and in some embodiments completely fill the cavity 34, as is shown in FIG. 5C.

The expandable implant 8 is substantially solid and stable at the first volume when inserted into the cavity 34. Any amount of time that is necessary can be used to place the expandable implant 8 within the cavity 34. Once in place the expandable material 10 is heated by the activated energy source 17 causing the polymeric matrix phase 12 to soften and allow the expandable gas source 14 to expand causing the expandable implant 8 to expand from its first stable volume to its second expanded volume within the cavity 34. After expansion, the energy source 17 can be turned off, removed, decoupled or otherwise prevented from supplying energy to the expandable material 10. For example, where the energy source 17 is coupled to the insertion instrument 38, the insertion instrument 38 can be removed from the cavity 34 in a manner that leaves the expandable implant 8 in situ in the cavity 34 after a sufficient amount of expansion has taken place. Once the energy source 17 has been removed or otherwise ceases to provide heat to the expandable material 10, the expandable material 10 cools and the expandable implant 8 becomes structurally rigid at the second expanded volume due to hardening of the polymer matrix 12.

Referring to FIGS. 6A-6C, the expandable implant 8 includes a number of expandable particles 21 as described in FIGS. 3A-3B above. In one example, the expandable implant 8 further includes a carrier material 26 that is mixed with the expandable particles 21 to form an implant body for delivery to a targeted anatomical cavity 34. As shown in FIG. 6A, an insertion instrument 38, such as a syringe, for example, is used to deliver the expandable implant 8 to a targeted cavity 34 in a bone 30. The insertion instrument 38 can also include an energy source 17 that is coupled to the insertion instrument 38, to provide energy sufficient to heat the expandable particles 21 similar to the embodiments discussed in FIGS. 5A-5D. Expandable implant 8 is positioned on a distal end of the insertion instrument 38, which is inserted into the cavity 34 of the bone 30 such that the expandable implant 8 is position in the cavity 34 at a first stable volume.

In FIG. 6B, energy source 17 has been activated, resulting in the expandable particles 21 expanding due to the heating of the expandable material 10 from the first state to the transition state. The polymer matrix 12 softens and expandable gas source 14 begins to grow, and the expandable implant 8 expands from a first stable volume. In FIG. 6C, the expandable particles 21 have all expanded and expandable implant 8 reaches a second expanded volume at a second temperature within the cavity 34. Similar to the example described in FIGS. 5A-5C above, after expansion of the expandable implant 10 reaches a desired second expanded volume, the energy source 17 can be removed or otherwise prevented from further heating the expandable material 10. As a result, the expandable particles 21 cool again, and form a structurally rigid expandable implant 8 at a second expanded volume due to hardening of the polymer matrix 12. In one embodiment, the polymer matrix 12 of adjacent particles 21 bond together during cooling to form a composite structure of bonded particles.

According to a further aspect of the present disclosure, a method is provided for filling an anatomical cavity including one or more, up to all, of the following steps:

inserting an expandable implant including an expandable material into an anatomical cavity, the material including a polymer matrix and an expandable gas source disposed within at least a portion of the matrix phase, the expandable implant having a stable first volume at a first temperature; and after the expandable implant is in place within the anatomical cavity, expanding the implant within the cavity by heating the expandable material to a second temperature to soften the matrix phase and allow expansion of the expandable gas source to expand the expandable implant to a second expanded volume greater than the first volume and provide an adaptation of the expandable implant to the anatomical cavity.

In another embodiment filling the cavity includes filling a spinal cavity in a vertebroplasty procedure.

FIGS. 7A-7C illustrate an alternative example of a system for filling an anatomical cavity utilizing an expandable implant 8 including an expandable material 10. In FIG. 7A, the expandable material 10 is heated from a first state to a transition state by an energy source prior to placement within the cavity 34 in the bone 30. After heating the expandable material 10 using any one of the previously described energy sources, an insertion instrument 38, for example a syringe, is used to place the expandable implant 8 into the cavity 34 as shown in FIG. 7A. In FIG. 7B, the instrument 38 can be removed leaving the expandable implant 8 in situ within the cavity 34. The expandable implant 8 proceeds to expand from a first stable volume to a second expanded volume. In FIG. 7C, the expandable material has reached a second state and the expandable implant 8 is shown in a second expanded stated within cavity 34.

According to an alternative aspect of the present disclosure, a method is provided for filling an anatomical cavity including one or more, up to all, of the following steps:

heating an expandable implant including an expandable material having a stable first volume at a first temperature to a second temperature, the expandable material including a polymer matrix and an expandable gas source disposed within at least a portion of the matrix phase, wherein the polymer matrix softens at the second temperature, inserting the expandable implant into an anatomical cavity; and expanding the implant within the cavity by expansion of the expandable material to expand the expandable implant to a second expanded volume greater than the first volume and provide an adaptation of the expandable implant to the anatomical cavity.

In still another embodiment according to the disclosure, the expandable implant can also be formed into a bone fixation device. Bone fixation can include, for example, a screw, a nail, a Kirschner wire, etc. Referring to FIG. 8A expandable implant 8 is an expandable intramedullary fixation member that can be used to secure a fracture in a long bone of a mammal, for example, a human femur. In the example shown in FIG. 8A, expandable implant 8 includes an expandable material 10 having a plurality of expandable gas sources 14 embedded within the polymer matrix 12 where the expandable gas sources 14 are concentrated in selected concentrated regions 41 and 42. Other embodiments can include more or less than two regions as desired, as well as including a more or less homogenous distribution of expandable gas sources than is shown here. The expandable implant 8 can further include regions 43 that are devoid of gas sources 14, or has a reduced concentration of gas sources.

FIG. 8B shows the expandable implant after an activated energy source 17 has been applied to the expandable implant 8 causing expansion of the expandable gas sources 104 at the first 41 and second 42 concentrated regions. The activated energy source 17 does not cause the region 43 devoid of gas sources 14 to expand, or alternatively if the region 43 includes a reduced concentration of gas sources, the activated energy source 17 can cause the region 43 to expand less than the concentrated regions 41 and 42. For example, in FIG. 8B a beam of light such as a laser can act as the energy source 17. Laser energy 17 is shown passing down a length of the expandable implant and selectively heating and expanding the first concentrated region 41 and the second concentrated region 42. In one embodiment, a sensitizer such as a dye is further included at the first concentrated region 41 and the second concentrated region 42 to react with the laser energy 17. FIG. 8B shows the expandable implant 8 having a second expanded volume at the first concentrated region 41 and the second concentrated region 42. The expansion that results in the first 41 and second 42 concentrated regions of the expandable implant 8 can enable the expandable implant 8 to grip the bone in two or more locations to hold a fracture in place.

Figures 9A, 9B:
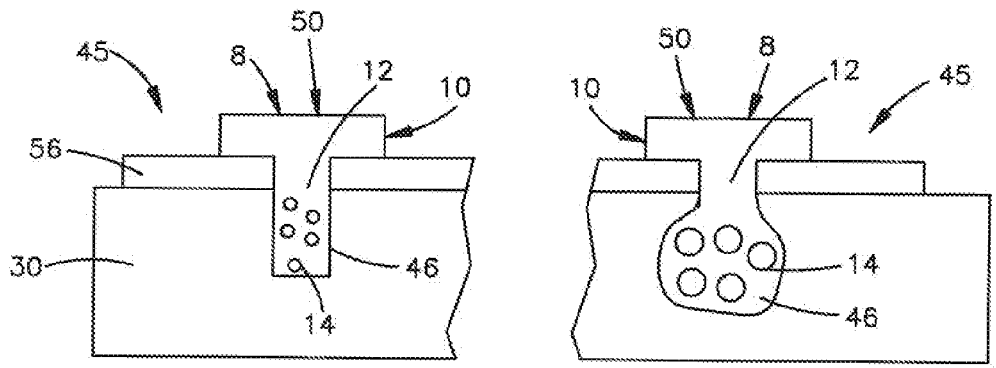
FIG. 9A is a side elevation view of a bone fixation device including an expandable implant according to one embodiment and an auxiliary implant such as a bone plate, prior to expansion of the expandable implant.
FIG. 9B is a side elevation view of the bone fixation device illustrated in FIG. 9A after expansion of the expandable implant.

Referring to FIGS. 9A-B, the implant system 45 can further include a bone fixation device 50 that, in turn, can include at least one or both an auxiliary implant 56, and the expandable implant 8 which can be referred to as a first implant. The expandable implant 8 can be formed from an expandable material 10 having a polymer matrix 12 with a concentrated distribution of expandable gas sources 14 as described above. In the example shown, the expandable gas source 14 is concentrated only in a concentrated region 46 where expansion is desired. Expandable implant 8 is shown in a first stable volume prior to activation of the expandable material 10. The bone fixation device 50 can further include the auxiliary implant 56, for example a bone plate, where expandable implant 8 can fix, or provide secondary fixation of the auxiliary implant 56 to a portion of a bone 30. FIG. 12 also shows the expandable implant 8 after activation by an energy source of the expandable material 10 from a first stable state to a second expanded state, as described in embodiments above. The concentrated region 46 of expandable implant 8 is shown in a second expanded volume. While the expandable implant 8 shown in FIG. 12 includes only a single concentrated region 16 for expansion, the expandable implant can include any number of regions for expansions as desired.

Figures 10A, 10B:
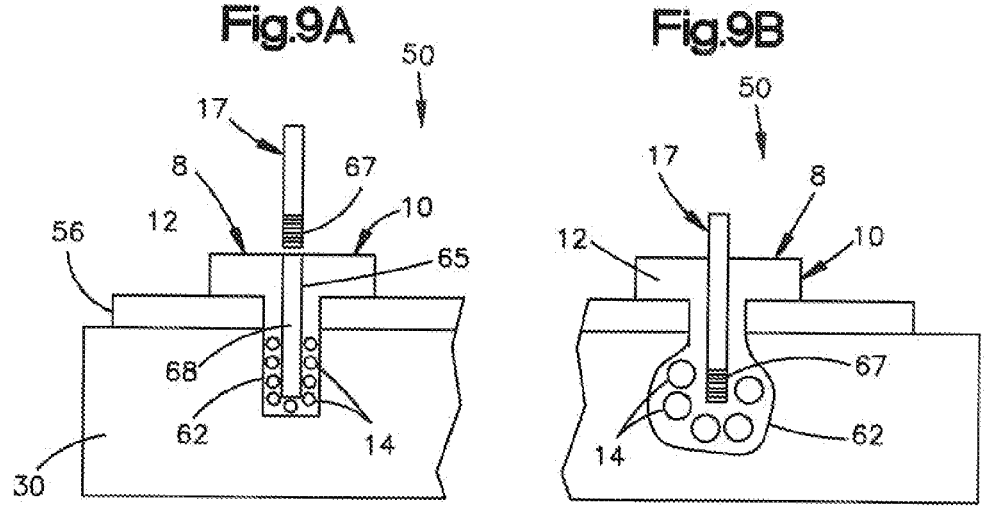
FIG. 10A is a side elevation view of a bone fixation device including an expandable implant according to another embodiment and an auxiliary implant such as a bone plate, and further including and insertable energy source, wherein the expandable implant is illustrated prior to expansion.
FIG. 10B is a side elevation view of a bone fixation device as illustrated in FIG. 10A, after expansion of the expandable implant.
Figure 13:
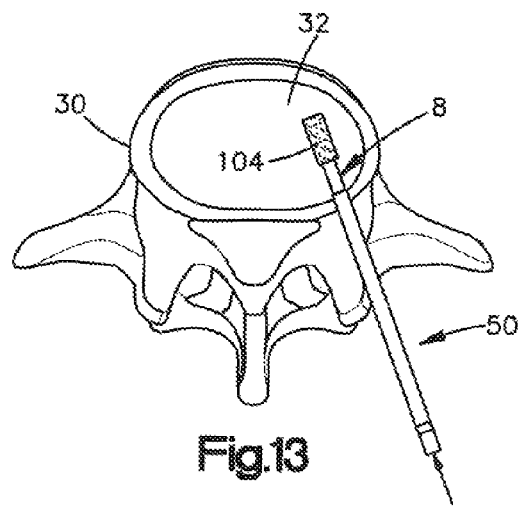
FIG. 13 is a top elevation view of the bone fixation device of FIGS. 12A-12B in place in a vertebra according to one embodiment.

Referring to FIGS. 10A-B, the implant system 45 is illustrated as including the bone fixation device 50 and the energy source 17. The bone fixation device 50 includes, according to the illustrated embodiment, includes an expandable implant 8 formed from an expandable material 10 having a polymer matrix 12 with a distribution of expandable gas sources 14. As illustrated, the expandable gas source 14 is concentrated only in a region 62 where expansion is desired. The expandable implant 8 is shown in a first stable volume prior to activation of the expandable material 10. The auxiliary implant 56, is illustrated a bone plate or any alternative implant, such that the expandable implant 8 can fix the auxiliary implant 56 to a portion of a bone 30. It should be appreciated that the implant 8 can provide primary or secondary fixation to the auxiliary implant 56 as desired. The implant 8 further includes an interior wall 65 that peripherally defines a cavity 68 formed within the expandable implant 8. Cavity 68 can be shaped to accept an insertable energy source 17 having an energy emitting tip 67, for example, a heat emitting tip. FIG. 10 also shows the expandable implant 8 after activation of the expandable material 10 by the energy source 17. The insertable energy source 17 is placed into the cavity 68 and a tip 67 is heated, for example by resistive heating, although any suitable energy source as previously described can be used to activate the expandable material 10. After activation of the expandable material 10 to a second expanded state, region 62 of expandable implant 8 is shown in a second expanded volume. While expandable implant 8 shown in FIG. 13 illustrates only a single region 62 for expansion, the expandable implant 8 can include any number of regions for expansions as desired.

Figure 11:
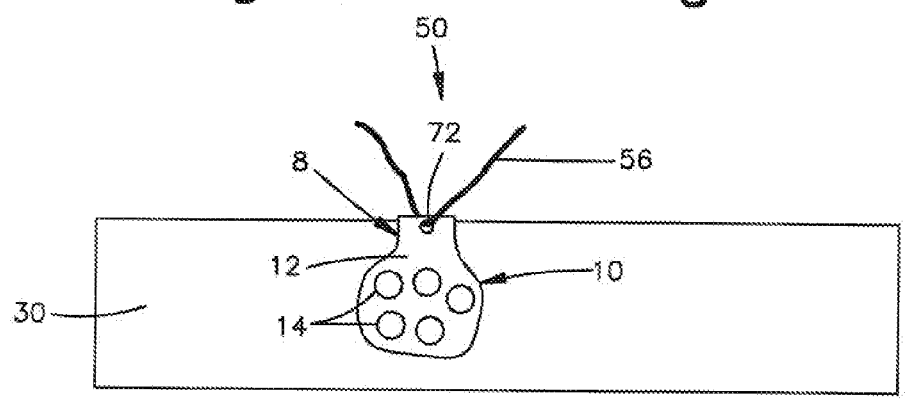
FIG. 11 is a side elevation view of a bone fixation device including an expandable implant according to one embodiment and an auxiliary implant such as a suture.

Referring to FIG. 11, the bone fixation device 50 is illustrated as including an expandable implant 8 and an auxiliary implant 56, which is illustrated as a suture. The expandable implant 8 is illustrated as formed from an expandable material 10 having a polymer matrix 12 with a distribution of expandable gas sources 14. Expandable implant 8 as shown has already been expanded to a second expanded volume and fastened in a portion of a bone 30. The bone fixation device 50 can includes a hole 72 or other suitable fastening configuration to hold the suture 56. In some procedures a suture is more adaptable to securing devices other than bone plates to the bone 30.

Referring to FIG. 12A, the fixation device 50 is configured as a Kirschner wire. For instance, the auxiliary implant 56 includes an auxiliary implant body 83 that defines opposed first 86 and second 87 ends and an interior passage 91 peripherally defined by an inner wall 93 and extending substantially the entire length of the auxiliary implant body 83 from first end 86 to second end 87. The fixation device 50 can include a tip 89 (schematically illustrated in FIGS. 14A-D) disposed proximate to the second end 87, and can include all or a portion of the expandable implant 8 and the auxiliary implant 56, alone or in combination. The auxiliary implant 56 define a first end opening 94 to the passage 91 at the first end 86 of the auxiliary implant body 83, and a second end opening 97 to the passage at the second end 87 of the auxiliary implant body 83. The expandable implant 8 includes expandable material 10 and has an implant body 9 shaped as an insert to fit within passage 91. The expandable implant 8 shown includes a first portion 101 including the expandable material 10 and substantially transparent, and a second portion 104 including the expandable material 10 and further including sensitizer such as a dye contained within it. Auxiliary body 83 can be formed from any suitable biocompatible material as desired and can include, for example, any number of biocompatible metals, or other structurally solid implantable materials such as polymers, ceramics, etc. Suitable metals can include stainless steel, titanium, or other biocompatible metals. In one embodiment the expandable implant 8 can be retracted such that it is contained wholly within passage 91. In another embodiment, for example as shown in FIG. 12A, the expandable implant 8 can travel through the passage 91, before, after, or during expansion, beyond the first end opening 94 or the second end opening 97 or both. The expandable implant in FIG. 12A is at a first stable volume prior to activation of the expandable implant material 10.

In one example as shown in FIG. 12 A, all or part of the dyed second portion 104 of the expandable implant 8 is extended beyond the second end opening 97 of the auxiliary body 83, and an energy source 17, for example a laser light, can be directed from a direction from the first end 86 of the auxiliary body 83 down a length of the first portion 101 of the expandable implant body 9 to the second dyed portion 104 at the second end 87 of the auxiliary body 83. FIG. 12B shows the bone fixation device 80 after exposure of the second dyed portion 104 of the expandable implant 8 to the energy source 17. Energy source 17 transmits energy to the second dyed portion 104, heating the expandable implant material 10 and softening the polymer matrix at the second dyed portion 104 and allowing the expandable gas source contained within the second dyed portion 104 to expand causing the expandable implant 8 to expand from a first stable volume to a second expanded volume at the second dyed portion 104 that extends beyond the second end 87 of the auxiliary body 83.

Although FIGS. 12A and 12B show activation of the expandable implant material 10 via using a light source and a dyed portion, other expandable material heating mechanisms such as resistance heating, ultrasonic friction, heat fluid transfer, chemical catalyst, etc. are possible. Laser heating of a dyed portion has the advantage of easily activating only a selected dyed portion of the expandable material insert 220. Although laser light is used as an example, other light sources, for example UV light, can be utilized as desired.

While the auxiliary body 83 of the auxiliary implant 56 is illustrated in FIGS. 12A-12B as having a passage 91 and a first 94 and second 97 end openings, the auxiliary body 83 is not so limited. Any number of openings can extend from the passage 91 of the auxiliary body 83, and in any desired orientation. The opening or openings of the auxiliary body 83 allow the expandable implant 8 to expand from a first stable volume to a second expanded volume that extends beyond the auxiliary body 83. One skilled in the art can appreciate any number of openings or their positioning along the auxiliary body 83 as desired.

Referring to FIG. 13, the fixation device 50 can be placed within a bone 30 such as a vertebral body. The dyed portion 104 of the expandable implant 8 is shown engaging an interior region 32 of the bone 30 after expansion of the expandable implant 8 to the second expanded volume. By extending the expandable implant 8 into the bone 30 relative to the auxiliary implant 56, and subsequently expanding the second dyed portion 104 as described above, the bone fixation device 50 is held securely in place. Prior fixation devices relied solely on friction of the sides of devices such as Kirschner wires to prevent movement of the devices. The expansion of the second dyed portion 104 of the expandable implant 8 provides a significant increase in preventing unwanted movement or motion of the device 50.

Referring now to FIGS. 14A-D, the tip 89 of the fixation device 50 illustrated in FIGS. 12A-B is illustrated in accordance with multiple embodiments. The expandable implant 8 includes an expandable implant material 10, one or more portions up to all of which can be dyed or transparent. The second end opening 97 allows the expandable implant 8 to expand at the second dyed portion at a dyed end 114 once the expandable material 10 is activated. The fixation device 50 includes a cutting edge 113 that, in turn, defines a second end opening 97. The tip 89 can be rotated inside bone such that the cutting edges 113 create an opening the bone that receives the bone fixation device 50. The tip 89 of the fixation device 50 can include a tapered end 117 to facilitate insertion. In accordance with the illustrated embodiment, the second end opening 97 is open at the pointed end 117, and is closed by the auxiliary implant body 83. In one example the second end 87 is made from a hardened material such as stainless steel, sufficient to hold the cutting edge 113. Once in place in the bone or other tissue, an energy source, for example laser light or other light source is passed down the length of the first transparent portion 101 of the expandable implant 8 to the dyed end 114 of the second dyed portion 104. Once activated by the laser light, the expandable material 10 at the dyed end 114 is heated and the expandable implant 8 expands at the dyed end 114 through the second opening 97 and secures the bone fixation device in place.

Figure 14A:
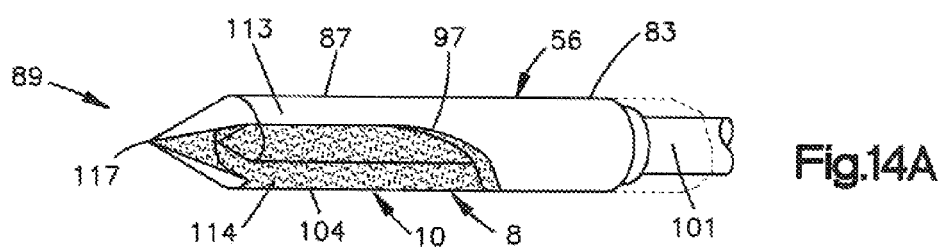
FIG. 14A is a side elevation view of a second end configuration for a bone fixation device of FIG. 12A-12B according to a further embodiment
Figure 14B:
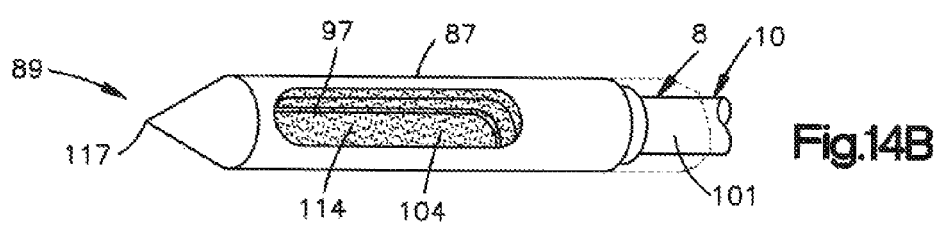
FIG. 14B is a side elevation view of the second end similar to the second end as illustrated in FIG. 14A but constructed in accordance with another embodiment.
Figure 14C:
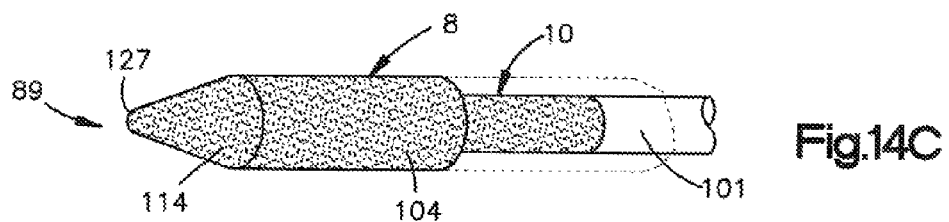
FIG. 14C is a side elevation view of the second end similar to the second end as illustrated in FIG. 14B but constructed in accordance with another embodiment.

Referring to FIG. 14B, the opening 97 can be enclosed by the auxiliary implant body 83, and thus does not extend into the tapered end 117. Thus, the bone fixation device 50 can define a cutting edge 113 as illustrated in FIG. 14A, or can be devoid of a cutting edge as illustrated in FIG. 14B. Alternatively still, the fixation device 50 can be devoid of an opening 97. The expandable material 10 at the dyed end 114 thus softens and expands such that dyed end 114 can move into the pores of the bone, and provides secure fixation to the bone. It should thus be appreciated that the dyed end 114 can likewise soften and expand in embodiments where the tip 89 includes an opening 97.

Figure 14D:
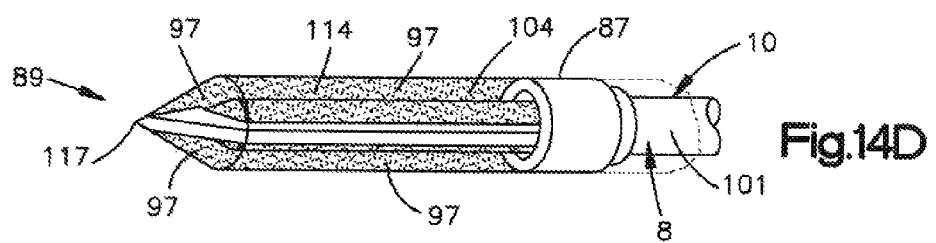
FIG. 14D is a side elevation view of the second end similar to the second end as illustrated in FIG. 14C but constructed in accordance with another embodiment.

Referring now to FIG. 14D, the tip 89 defines a plurality of second end openings 97 to allow expansion of the dyed end 114. Similar to the first example 110, the second end openings 97 of the fourth example 140 include cutting edges 113 to facilitate cutting of a hole in bone for insertion of the device. Multiple second end openings 97 allows for expansion of the dyed end 114 in multiple radial directions that are angularly offset with respect to each other. Such a configuration may provide increased pullout resistance in certain fixation procedures.

In an additional embodiment of the present disclosure, a method of fixing an bone fixation device within a hole is provided, including one or more, up to all, of the following steps:

inserting a bone fixation device into a hole, the bone fixation device including an auxiliary implant having a auxiliary body including a passage and at least one opening connecting to the passage, and wherein an expandable implant having an implant body and including an expandable material is at least partially contained within the passage;

transmitting energy from an energy source through a first portion of the expandable implant to a second portion of the expandable implant, wherein the first portion is substantially transparent and the second portion is a dyed portion including a sensitizer;

absorbing energy by the second dyed portion of the expandable implant to cause a heating of the second dyed portion; and, expanding the second dyed portion of the expandable implant from a first stable volume to a second expanded volume.

The method as described above can further include the step of extending the expandable implant from the at least one opening prior to the transmission of energy from an energy source. In another embodiment of the method as described, the energy source is a laser and the absorbing of energy is the absorbing of light to heat the second dyed portion. While the method as described can be used to fix a device within a bone, for example, it is also contemplated within the scope of the disclosure that the method can include fixing a device in other anatomical locations as desired. In operation the auxiliary implant is inserted into a hole. The expandable implant as described included the expandable material having an expandable gas source encased within a polymer matrix as described in the embodiments above. Due to the absorbing of energy, the second dyed portion is heated and the expandable material at that location is activated, causing a softening of the polymer matrix and allowing the expandable gas source to expand, expanding the expandable implant at the second dyed portion from a first stable volume to a second expanded volume.

Referring now to FIGS. 15-19, a bone fixation device is shown including an auxiliary implant having an auxiliary body and an expandable implant including an expandable material as described above. The expandable implant can be applied with the auxiliary implant so as to enhance (or provide) secondary stability for bone fixation device. The auxiliary implant can be any number of common medical implants, such as, for example, a nail or bone screw. The expandable implant can be placed at various places along the auxiliary body to enhance the secondary stability of the bone fixation device, or alternatively the expandable implant can be placed in a passage in the auxiliary implant where an opening or openings in the auxiliary body can allow for the outward expansion of the expandable implant.

Referring to FIG. 15, the bone fixation device 50 can be configured as a bone anchor, for instance configured as a screw or nail or the like, that defines a head 95 and a shaft 99 that extends from the head portion 95. The shaft 99 can be smooth, threaded, toothed, or otherwise textured as desired. Thus, the shaft 99 is configured to be driven into an underlying bone 30. As illustrated, the auxiliary implant 56 can define the head 95 and a first portion of the shaft 99, and the expandable implant 8 can define a second portion of the shaft 99, and can be coated onto an outer surface 153 of a tip 156 of the auxiliary implant body 83, or can otherwise extend from the tip 156 as desired. Referring to FIG. 16, the expandable implant 8 can be coated along a substantial entirety of the shaft 99. Thus, the expandable implant 8 can expand inside the bone 30 so as to fix the bone fixation device 50 to the bone 30 in the manner described above.

Referring to FIG. 17, the bone fixation device 50 can define an interior passage 91 that extends through the shaft 99 and terminates prior to the tip 156. The interior passage 91 can further extend through the head 95. The interior passage 91 can contain the expandable implant 8. The bone fixation device 50 can include at least one such as a plurality of radial perforations 157 that extend from the interior passage 91 and through the outer surface 153. Accordingly, the expandable implant 8 can expand, thereby fixing the fixation device 50 to the bone 30. It should be appreciated that the expandable implant 8 can be disposed in the interior passage 91 prior to expansion, such that the expandable implant 8 expands through the radial perforations 157. Alternatively, the expandable implant 8 can be injected into the passage 91 under sufficient pressure that causes portions of the expandable implant 8 to travel through the perforations 157 prior to expansion. As illustrated in FIG. 18, the interior passage 91 can further define a tip portion 159 that extends through the tip 156. Accordingly, the expandable implant 8 can further pass through the tip portion 159 in the manner described above with respect to the perforations 157. When the expandable implant 8 is expanded form its first stable volume to its second expanded volume and cools, it can form rigid clusters 158 along the outer surface 153 of the auxiliary implant 56 so that the stability of the anchoring of the bone fixation device 50 can be enhanced.

Referring to FIG. 19, the bone fixation device 50 includes an auxiliary implant 56 that can define a bone anchor that contains or otherwise is operatively coupled to the primary implant 8 in the manner described above, and can further include a second auxiliary implant 56' illustrated as a bone plate that is configured to receive the shaft 99 of the bone anchor.

While the bone fixation devices 50 illustrated in FIGS. 15-19 has been described in connection with insertion of the expandable implant 8 into the auxiliary implant 56, it should be appreciated that the expandable implant 8 can alternatively be injected directly into the bone 30. The auxiliary implant 56 can subsequently be driven into the bone 30 and the expandable implant 8, either prior to or after expansion and subsequent hardening of the expandable implant 8 inside the bone 30.

Referring to FIG. 20 a bone fixation device 50 includes an auxiliary implant 56 and an expandable implant 8. Auxiliary implant 56 is shaped substantially like a screw and includes a body 83 with threads 181 cut into the side of auxiliary body 83. A device engagement shape 183 such as a Philips head, hex head, Torx head, etc. is formed into a first end 86 of the auxiliary body 83 to engage a screwdriver or similar tool. The auxiliary implant 56 includes one or more passages 91 to allow for extension of an expandable implant 8 from the auxiliary body 83. Auxiliary body 83 is shown with two passages 91, extending from the first end 86 to a second end 87 and further including second end openings 97 at second end 87 of auxiliary body 83. As can be appreciated, more passages or fewer passages are within the scope of disclosure.

The body 9 of the expandable implant 8 can be configured as a wire that is sized to fit within each of the passages 91. Each body 9 can include an expandable end 188 that is outwardly displaced from the auxiliary implant 56. As described above, the expandable implant 8 can include a first portion 101 including the expandable material 10 and substantially transparent, and a second portion 104 including the expandable material 10 and further including sensitizer such as a dye contained within it. The second dyed portion 104 can be located at expandable ends 188 such that an energy source 17, for example, laser light, can be transmitted down the first transparent portion 101 of the expandable implant 8 and be absorbed at the expandable ends 188.

In operation, the device 50 is screwed into place at a targeted anatomical location, for example a bone, and then the expandable implants 8 are extended through passages 91 into a surrounding bone or tissue. The expandable ends 188 are then activated to expansion through the transmission of energy from energy source and further secure the device 50 in place to prevent unwanted movement such as unscrewing of the device 50 over time.

Referring to FIG. 21, the auxiliary body 83 can define a passage 91 that extends from the first end 86 to a second end 87, and at least one such as a plurality of radial perforations 157 that extend from the passage 91 through outer surface 153 of the device 50. During operation, the device 50 is driven into place, then an expandable implant 8 is inserted into the passage 91 with an expandable end 188 located adjacent to the radial perforation 157. The expandable end 188 is then activated to expansion by any of the previously described energy source mechanisms for example, a laser light passing down the expandable implant 8 to the expandable end 188 and interacting with a dyed portion at the end 188. The expandable end 188 then expands through the number of radial perforations 157 to a second expanded volume securing the device 50 from unwanted movement or rotation.

Referring to FIG. 22, the expandable implant 8 can be affixed to a side 153 of the auxiliary body 83 such that radial perforations 157 are radially inwardly disposed with respect to the expandable implant 8, which can be threaded as desired. During operation, the device 50 is driven into place, and then the expandable implant 8 is activated to expansion by any of the previously described energy source mechanisms. For example, laser light can be transmitted down passage 91 and through radial perforations 157 to heat the expandable material 10. In one example the expandable material 10 is activated to expansion by absorbing laser energy in a dyed portion of the expandable implant 8. As in other examples, expansion of the expandable implant 8 secures the device 50 from unwanted movement or rotation.

Referring to FIG. 23, the implant system 45 includes an energy device 13 illustrated as a laser that is configured to emit an energy source 17 in the form of a laser beam. The implant system 45 further includes a bone fixation device 50 configured as a bone anchor that includes an expandable implant 8 and an auxiliary implant 56 as described above. The auxiliary implant 56 can be configured as a hip screw that is threaded into a hip bone 30 to secure portions of a hip joint across a fracture. Once the auxiliary implant 56 is in place, one or more expandable implants 8 extend out from the auxiliary implant 56 from an internal passage of the auxiliary implant 56 in the manner described above.

The expandable implant 8 can define a plurality of expandable ends 188 that extend out the auxiliary implant 56. The implant system 45 can further include a second auxiliary device 56' that can be configured as a bone plate or any suitable alternatively constructed implant. As illustrated, the bone plate receives the bone anchor which is fixed in underlying bone 30. The implant system 45 can further include an optical lens 193 that can shape the laser beam 17. For instance the lens 193 can focus the laser beam 17 down a length of the expandable implant 8 to the expandable ends 188, thereby activating the expandable material 10 of the implant 8 in the manner descried above. In accordance with the illustrated embodiment, the laser beam 17 causes the temperature of the expanding end 188 to increase and expand to the second expanded volume so as to secure the expandable implant 8 in the bone 30. As illustrated in FIG. 24, the fixation device 50 can include one or more conventional anchors 198 that further fix that bone plate 56' to the underlying bone 30.

Referring now to FIG. 25 the bone fixation device 50 includes an auxiliary implant 56 that can be integrally or discretely connected to a second auxiliary implant 56' that can be shaped as desired and subsequently fastened to tan underlying bone via one or more conventional anchors 198. The bone fixation device 50 further includes one or more expandable implants 8 that define respective expanding ends 188 in the manner described above.

Referring now to FIGS. 26-27, the bone fixation device 50 can be provided as an intramedullary fixation member illustrated as an intramedullary nail that includes an auxiliary implant 56 whose outer surface 153 is at least partially covered by the expandable implant 8. Thus, the expandable implant 8 can provide internal locking or fixation of the auxiliary implant 56 in the intramedullary canal 32 of the bone 30. The expandable implant 8 can be used for distal and/or proximal locking of the auxiliary implant 56 within a long bone 30 as illustrated in FIG. 26. Alternatively, part or all of the outer surface 153 of the auxiliary implant 56 can be coated with the expandable implant 8 as illustrated in FIG. 27, such that the auxiliary implant 56 can be inserted and removed without substantial force because the nail diameter is smaller than the diameter of the intramedullary canal 32. The intramedullary nail can be easily removed from the bone 30 by re-heating the expandable implant 8, thereby softening the implant body 9 and facilitating movement of the intramedullary nail within the intramedullary canal 32.

It should be appreciated that the expandable implant 8 can provide fixation of the intramedullary nail within an intramedullary canal 32 the bone 30 without the use of locking screws and corresponding secondary incisions. Further, the intramedullary nail can be implanted without the use of auxiliary aiming devices for locking holes. Of course, it should be appreciated that locking screws, corresponding secondary incisions, and/or auxiliary aiming devices can be used if desired.

Referring now to FIGS. 28-32, the bone fixation device 50 is configured as an intramedullary fixation device, constructed in accordance with an alternative embodiment that is disposed in an intramedullary canal 32 of a bone 30 to secure a fracture 201. The auxiliary implant 56 is configured as an intramedullary stent that includes a structural expandable mesh 205 such as a metal mesh or a polymer mesh. The expandable implant 8 is disposed within an interior opening 207 defined by the expandable mesh 205 across a fracture line 201 in the bone 30 at a first stable volume as shown in FIGS. 28 and 30.

During operation, the bone fixation device 50 is placed in the intramedullary canal 32 of the bone 30 so as to span across the fracture 201 as shown in FIG. 28. The expandable implant 8 is then activated to expansion by transmission of energy from an energy source as described above. The mesh 205 then expands as a result of an expansion force provided by the expandable implant 8 as the expandable implant 8 expands from the first stable volume to the second expanded volume. The bone fixation device 50 can thus expand to fill the intramedullary canal 32 of the bone 30 to reduce fracture 201 as shown by FIGS. 29 and 31. Over time, as shown by FIG. 32, the expandable implant 8 can resorb, while the bone fixation device 50 can remain in the expanded state.

Although the present disclosure has been described in accordance with several embodiments, it should be understood that various changes, substitutions, and alterations can be made herein without departing from the spirit and scope of the present disclosure, for instance as indicated by the appended claims. Thus, it should be appreciated that the scope of the present disclosure is not intended to be limited to the particular embodiments of the process, machine, manufacture, and composition of matter, methods and steps described herein. For instance, the various features as described above in accordance with one embodiment can be incorporated into the other embodiments unless indicated otherwise. Furthermore, as one of ordinary skill in the art will readily appreciate from the present disclosure, processes, machines, manufacture, composition of matter, methods, or steps, presently existing or later to be developed that perform substantially the same function or achieve substantially the same result as the corresponding embodiments described herein may be utilized according to the present disclosure.

It will be appreciated by those skilled in the art that various modifications and alterations of the invention can be made without departing from the broad scope of the appended claims. Some of these have been discussed above and others will be apparent to those skilled in the art.

The invention claimed is:

1. A method of filling an anatomical cavity comprising:
    inserting an expandable implant into an anatomical cavity, the implant including a polymer matrix and an expandable gas source encapsulated within at least a portion of the polymer matrix, the implant defining a first volume at a first temperature below the glass transition temperature of the polymer matrix; and
    transmitting energy from an energy source to the expandable implant, wherein the polymer matrix is heated from the first temperature to a second temperature above its glass transition temperature so as to soften the polymer matrix; and,
    expanding the expandable gas source to expand the expandable implant to a second expanded volume greater than the first volume.

2. The method according to claim 1, wherein the heating step is performed after the expandable implant is inserted into the anatomical cavity.

3. The method according to claim 1, wherein the heating step is performed before the expandable implant is inserted into the anatomical cavity.

4. The method according to claim 1, wherein the expandable implant is configured to adapt to the contour of the anatomical cavity after the heating step.

5. The method according to claims 1, further comprising the step of coating the expandable implant onto at least a portion of an outer surface of an insertion instrument.

6. The method according to claim 1, wherein the expandable implant includes concentrated regions of the expandable gas source such that expanding the expandable gas source to expand the expandable implant to a second expanded volume occurs only at the concentrated regions.

7. The method according to claim 1, wherein the expandable implant includes a dyed region such that transmitting energy from an energy source to the polymer matrix so as to heat the polymer matrix occurs only at the dyed region.

8. The method according to claim 1, wherein the expandable implant is in the form of a fixation device.

9. The method according to claim 8, wherein the fixation device is in the form of an intramedullary nail.

10. The method according to claim 8, further comprising fixing an auxiliary implant to or within a bone with the fixation device.

11. The method according to claim 10, wherein the auxiliary implant defines an auxiliary implant body configured as a bone anchor.

12. The method according to claim 11, wherein the expandable implant is coated onto or affixed to an outer surface of the auxiliary implant body.

13. The method according to claim 11, wherein the expandable implant is disposed within a passage of the auxiliary implant body.

14. The method according to claim 13, wherein the auxiliary implant body is configured as a bone screw.

15. The method according to claim 12, wherein the auxiliary implant body is configured as a Kirschner wire.

16. The method according to claim 10, wherein the auxiliary implant is a bone plate.

* * * * *